United States Patent
Obradovich

(10) Patent No.: US 9,571,449 B2
(45) Date of Patent: Feb. 14, 2017

(54) TECHNIQUE FOR OPERATING A VEHICLE EFFECTIVELY AND SAFELY

(71) Applicant: Auto Director Technologies, Inc., Las Vegas, NV (US)

(72) Inventor: Michael L. Obradovich, San Clemente, CA (US)

(73) Assignee: Auto Director Technologies, Inc., Las Vegas, NV (US)

( * ) Notice: Subject to any disclaimer, the term of this patent is extended or adjusted under 35 U.S.C. 154(b) by 0 days.

(21) Appl. No.: 14/133,548

(22) Filed: Dec. 18, 2013

(65) Prior Publication Data

US 2014/0107894 A1 Apr. 17, 2014

Related U.S. Application Data

(63) Continuation of application No. 13/042,304, filed on Mar. 7, 2011, now Pat. No. 8,626,382, which is a
(Continued)

(51) Int. Cl.
*G06F 7/00* (2006.01)
*H04L 29/12* (2006.01)
(Continued)

(52) U.S. Cl.
CPC ........... *H04L 61/2553* (2013.01); *G06F 7/00* (2013.01); *G06F 17/30315* (2013.01); *H04L 43/08* (2013.01)

(58) Field of Classification Search
USPC .............. 701/1, 36, 400, 487, 538; 715/700; 345/650, 661, 676, 501, 520
See application file for complete search history.

(56) References Cited

U.S. PATENT DOCUMENTS 3,582,926 A 6/1971 Hassan
4,314,232 A 2/1982 Tsunoda
(Continued)

FOREIGN PATENT DOCUMENTS

EP 0766811 4/1997
EP 0771686 5/1997
(Continued)

OTHER PUBLICATIONS

Notice of Reasons for Rejection from Japanese Patent Office (JPO) for related Japanese patent application (2002-528838) dated Feb. 16, 2010.
(Continued)

*Primary Examiner* — Rami Khatib
(74) *Attorney, Agent, or Firm* — Klein, O'Neill & Singh, LLP

(57) ABSTRACT

A control system is employed in a vehicle to assist a user to operate the vehicle effectively and safely. In accordance with the invention, the system provides driving assistance to the user by taking into account the user's physical condition, the vehicle condition and the surrounding conditions. The surrounding conditions include, e.g., road, weather and traffic conditions, external to the vehicle. The vehicle condition concerns the conditions of the brakes, steering, tires, radiator, etc. of the vehicle. Signs of fatigue, stress and illness of the user are monitored by the control system to assess the user's physical condition.

15 Claims, 15 Drawing Sheets

Related U.S. Application Data continuation of application No. 11/837,393, filed on Aug. 10, 2007, now Pat. No. 7,902,969, which is a continuation of application No. 11/226,513, filed on Sep. 13, 2005, now Pat. No. 7,417,531, which is a continuation of application No. 10/380,449, filed as application No. PCT/US01/29425 on Sep. 20, 2001, now Pat. No. 6,982,635.

(60) Provisional application No. 60/234,134, filed on Sep. 21, 2000, provisional application No. 60/283,685, filed on Apr. 13, 2001.

(51) Int. Cl.
  *G06F 17/30* (2006.01)
  *H04L 12/26* (2006.01)

(56) References Cited

U.S. PATENT DOCUMENTS

| | | |
|---|---|---|
| 4,334,215 A | 6/1982 | Frazier et al. |
| 4,401,848 A | 8/1983 | Tsunoda |
| 4,407,564 A | 10/1983 | Ellis |
| 4,419,730 A | 12/1983 | Ito et al. |
| 4,481,584 A | 11/1984 | Holland |
| 4,536,739 A | 8/1985 | Nobuta |
| 4,582,389 A | 4/1986 | Wood et al. |
| 4,636,782 A | 1/1987 | Nakamura et al. |
| 4,695,823 A | 9/1987 | Vernon |
| 4,716,458 A | 12/1987 | Heitzman et al. |
| 4,731,769 A | 3/1988 | Schaefer et al. |
| 4,740,779 A | 4/1988 | Cleary et al. |
| 4,740,780 A | 4/1988 | Brown et al. |
| 4,752,824 A | 6/1988 | Moore |
| 4,795,223 A | 1/1989 | Moss |
| 4,818,048 A | 4/1989 | Moss |
| 4,827,520 A | 5/1989 | Zeinstra |
| 4,837,551 A | 6/1989 | Iino |
| 4,876,594 A | 10/1989 | Schiffman |
| 4,909,074 A | 3/1990 | Gerresheim et al. |
| 4,914,705 A | 4/1990 | Nigawara |
| 4,926,171 A | 5/1990 | Kelley |
| 4,931,930 A | 6/1990 | Shyu et al. |
| 4,988,976 A | 1/1991 | Lu |
| 4,995,258 A | 2/1991 | Frank |
| 4,996,959 A | 3/1991 | Akimoto |
| 5,006,829 A | 4/1991 | Miyamoto et al. |
| 5,043,736 A | 8/1991 | Darnell et al. |
| 5,051,735 A | 9/1991 | Furukawa |
| 5,070,323 A | 12/1991 | Iino et al. |
| 5,119,504 A | 6/1992 | Durboraw, III |
| 5,122,796 A | 6/1992 | Beggs et al. |
| 5,173,881 A | 12/1992 | Sindle |
| 5,198,797 A | 3/1993 | Daidoji |
| 5,214,413 A | 5/1993 | Okabayashi et al. |
| 5,214,707 A | 5/1993 | Fujimoto et al. |
| 5,214,793 A | 5/1993 | Conway et al. |
| 5,235,633 A | 8/1993 | Dennison et al. |
| 5,239,700 A | 8/1993 | Guenther et al. |
| 5,257,190 A | 10/1993 | Crane |
| 5,270,689 A | 12/1993 | Hermann |
| 5,274,560 A | 12/1993 | La Rue |
| 5,278,532 A | 1/1994 | Hegg et al. |
| 5,293,115 A | 3/1994 | Swanson |
| 5,299,132 A | 3/1994 | Wortham |
| 5,334,974 A | 8/1994 | Simms et al. |
| 5,335,276 A | 8/1994 | Thompson et al. |
| 5,335,743 A | 8/1994 | Gillbrand et al. |
| 5,345,817 A | 9/1994 | Grenn et al. |
| 5,351,041 A | 9/1994 | Ikata et al. |
| 5,361,165 A | 11/1994 | Stringfellow et al. |
| 5,371,510 A | 12/1994 | Miyauchi et al. |
| 5,400,045 A | 3/1995 | Aoki |
| 5,404,443 A | 4/1995 | Hirata |
| 5,408,686 A | 4/1995 | Mankovitz |
| 5,414,439 A | 5/1995 | Groves et al. |
| 5,422,565 A | 6/1995 | Swanson |
| 5,432,904 A | 7/1995 | Wong |
| 5,440,428 A | 8/1995 | Hegg et al. |
| 5,442,553 A | 8/1995 | Parillo |
| 5,450,321 A | 9/1995 | Crane |
| 5,450,329 A | 9/1995 | Tanner |
| 5,450,613 A | 9/1995 | Takahara et al. |
| 5,453,740 A | 9/1995 | Gallagher et al. |
| 5,461,357 A | 10/1995 | Yoshioka et al. |
| 5,475,399 A | 12/1995 | Borsuk |
| 5,479,482 A | 12/1995 | Grimes |
| 5,483,632 A | 1/1996 | Kuwamoto et al. |
| 5,483,827 A | 1/1996 | Kulka et al. |
| 5,486,840 A | 1/1996 | Borrego et al. |
| 5,493,658 A | 2/1996 | Chiang et al. |
| 5,497,271 A | 3/1996 | Mulvanny et al. |
| 5,497,339 A | 3/1996 | Bernard |
| 5,504,622 A | 4/1996 | Oikawa et al. |
| 5,506,595 A | 4/1996 | Fukano et al. |
| 5,511,724 A | 4/1996 | Freiberger et al. |
| 5,519,403 A | 5/1996 | Bickley et al. |
| 5,519,410 A | 5/1996 | Smalanskas et al. |
| 5,521,579 A | 5/1996 | Bernhard |
| 5,521,580 A | 5/1996 | Kaneko et al. |
| 5,523,559 A | 6/1996 | Swanson |
| 5,525,977 A | 6/1996 | Suman |
| 5,528,248 A | 6/1996 | Steiner et al. |
| 5,528,496 A | 6/1996 | Brauer et al. |
| 5,534,888 A | 7/1996 | Lebby et al. |
| 5,539,869 A | 7/1996 | Spoto et al. |
| 5,543,789 A | 8/1996 | Behr et al. |
| 5,553,661 A | 9/1996 | Beyerlein et al. |
| 5,555,172 A | 9/1996 | Potter |
| 5,555,286 A | 9/1996 | Tendler |
| 5,555,502 A | 9/1996 | Opel |
| 5,559,520 A | 9/1996 | Barzegar et al. |
| 5,572,204 A | 11/1996 | Timm et al. |
| 5,576,724 A | 11/1996 | Fukatsu et al. |
| 5,579,535 A | 11/1996 | Orlen et al. |
| 5,596,319 A | 1/1997 | Spry |
| 5,619,412 A | 4/1997 | Hapka |
| 5,621,252 A | 4/1997 | Bucknam |
| 5,627,510 A | 5/1997 | Yuan |
| 5,627,547 A | 5/1997 | Ramaswamy et al. |
| 5,629,669 A | 5/1997 | Asano et al. |
| 5,638,305 A | 6/1997 | Kobayashi et al. |
| 5,648,769 A | 7/1997 | Sato et al. |
| 5,650,929 A | 7/1997 | Potter et al. |
| 5,654,715 A | 8/1997 | Hayashikura et al. |
| 5,666,102 A | 9/1997 | Lahiff |
| 5,670,953 A | 9/1997 | Satoh et al. |
| 5,684,490 A | 11/1997 | Young et al. |
| 5,689,252 A | 11/1997 | Ayanoglu et al. |
| 5,691,695 A | 11/1997 | Lahiff |
| 5,702,165 A | 12/1997 | Koibuchi |
| 5,708,584 A | 1/1998 | Doi et al. |
| 5,712,640 A | 1/1998 | Andou et al. |
| 5,726,688 A * | 3/1998 | Siefert .................. G06F 3/0482 715/808 |
| 5,734,336 A | 3/1998 | Smithline |
| 5,734,973 A | 3/1998 | Honda |
| 5,752,754 A | 5/1998 | Amitani et al. |
| 5,757,359 A | 5/1998 | Morimoto et al. |
| 5,758,311 A | 5/1998 | Tsuji et al. |
| 5,764,139 A * | 6/1998 | Nojima ................ G07C 5/0825 340/438 |
| 5,777,394 A | 7/1998 | Arold |
| 5,790,973 A | 8/1998 | Blaker et al. |
| 5,808,728 A | 9/1998 | Uehara |
| 5,913,241 A | 6/1999 | Ohashi et al. |
| 5,917,405 A | 6/1999 | Joao |
| 5,969,640 A | 10/1999 | Timm et al. |
| 6,006,161 A | 12/1999 | Katou |
| 6,014,608 A | 1/2000 | Seo |
| 6,021,956 A | 2/2000 | Haraguchi |
| 6,029,110 A * | 2/2000 | Zuber .................... B60K 35/00 701/1 |
| 6,161,071 A | 12/2000 | Shuman et al. |

(56) References Cited

U.S. PATENT DOCUMENTS

| | | | |
|---|---|---|---|
| 6,211,784 B1 | 4/2001 | Nishide | |
| 6,441,728 B1 | 8/2002 | Dixit et al. | |
| 6,546,002 B1* | 4/2003 | Kim | H04M 1/72525 |
| | | | 370/351 |
| 6,566,999 B2 | 5/2003 | Iwasaki et al. | |
| 6,624,749 B1* | 9/2003 | Winterkorn | B60K 37/02 |
| | | | 340/425.5 |
| 6,646,592 B2 | 11/2003 | Matsuoka | |
| 6,728,531 B1* | 4/2004 | Lee | G01C 21/34 |
| | | | 455/414.1 |
| 6,856,820 B1* | 2/2005 | Kolls | B60R 25/04 |
| | | | 340/853.1 |
| 7,765,058 B2* | 7/2010 | Doering | B60R 16/0236 |
| | | | 340/425.5 |
| 2001/0022551 A1 | 9/2001 | Barnett | |
| 2002/0070852 A1* | 6/2002 | Trauner | B60R 16/0373 |
| | | | 340/438 |
| 2004/0036622 A1* | 2/2004 | Dukach | G06Q 30/02 |
| | | | 340/691.6 |
| 2004/0254886 A1* | 12/2004 | Siepen | G07B 15/063 |
| | | | 705/51 |
| 2006/0190822 A1* | 8/2006 | Basson | G06Q 10/10 |
| | | | 715/700 |
| 2007/0124043 A1* | 5/2007 | Ayoub | G06F 21/10 |
| | | | 701/36 |
| 2007/0124044 A1* | 5/2007 | Ayoub | G06F 21/10 |
| | | | 701/36 |
| 2007/0124045 A1* | 5/2007 | Ayoub | G06F 21/10 |
| | | | 701/36 |
| 2007/0124046 A1* | 5/2007 | Ayoub | G06F 21/10 |
| | | | 701/36 |
| 2009/0069953 A1* | 3/2009 | Hale | B60W 50/08 |
| | | | 701/1 |
| 2009/0306883 A1* | 12/2009 | Faenger | G01C 21/3638 |
| | | | 701/532 |

FOREIGN PATENT DOCUMENTS

| | | |
|---|---|---|
| JP | 11-120478 | 4/1999 |
| JP | 11-195198 | 7/1999 |
| WO | WO 97/13657 | 4/1997 |

OTHER PUBLICATIONS

"Look, Ma, No Hands!" Autoweek, Headliner, Apr. 27, 1997 (p. 6).
Adcock, "No Longer Square," Automotive & Transportation Interiors, Aug. 1996 (pp. 38-40).
Adcock, "Geneva Gems Blend Function and Designs," Automotive & Transportation Interiors, Interiors, May 1997, (pp. 52, 54 & 55, 38, 40, 41, 44).
Braunstein, "Airbag Technology Takes Off," Automotive & Transportation Interiors, Aug. 1996, (p. 16).
Braunstein, "Safety Gets Smarter," Automotive & Transportation Interiors, May 1997, (pp. 30-32, 36, 38, 40, 41 and 44).
Creasy, "Young at Art," Automotive & Transportation Interiors, May 1997, (pp. 24-6 & 28).
Heuchert, Eyes Forward: An Ergonomic Solution to Driver Information Overload,: Society of Automobile Engineering, Sep. 1996, (pp. 27-31).
Jackson, "Luxury, Versatility Highlight Students' Dream Vehicles," Mar. 31, 1997 (p. 26D).
Jewett, "Boss' Kettering Awards Honor GM Innovators," Automotive News, Mar. 31, 1997.
Jewett, "New ABS Provides quicker Emergency Stop," Automotive News, Apr. 21, 1997 (p. 24).
Kraar, "Knowledge Engineering," Fortune, Oct. 28, 1996, (pp. 163-164).
Krebs, "Cars That Tell You Where to Go," the New York Times, Dec. 15, 1996, Section 11, (p. 1).
Lapham, "Buick Experiments with Hands Free Driving," Automotive News, Apr. 21, 1997, (p. 60).
Lapham, "Its Not Hard to Get Used to Magnets Doing the Steering," Automotive News, Apr. 21, 1997, (p. 60).
Leutzbach et al., "Technical Evaluation of Collision Avoidance System," Automotive Electronics, The 1980's, 1983, Society of Automotive Engineers (pp. 427-435).
Numazawa, "Automotive Electronics in Passenger Cars," Automotive Electronics, the 1980's, Society of Automotive Engineers, 1988, (pp. 789-802).
Numazawa, "Overview and Future Plan of Automotive Electronic Systems," Automotive Electronics, The 1980's, Society of Automotive Engineers, 1986, (pp. 627-642).
Ott, "Special Exhibit Shows of Devices for Disabled Drivers," Automotive News, Mar. 24, 1997, (p. 4).
Rivard, "Automotive Electronics of the Year 2000," Automotive Electronics, The 1980's, 1986, Society of the Automotive Engineers, (pp. 567-584).
Sedgwick, "M-B, BMW Consider Adaptive Cruise Control," Automotive News, Mar. 17, 1997, (p. 6).
Stone, "Get Ready to Take a Back Seat to a Circuit Board," Newsweek, Jun. 2, 1997 (p. 10).
Takehana et al., "Millimeter-Wave Radars for Automotive Use," Automotive Electronics, the 1980's, Society of Automotive Engineers, 1988, (pp. 773-787).
Treece, "New Crop of Gadgets Promises Healthy, Comfy Ride," Automotive News, May 26, 1997, (pp. 3 & 49).
Yokoya et al., "Toyota Electronic Modulated Suspension (TEMS) System for the 1983 Soarer," Automotive Electronics, the 1980's, Society of the Automotive Engineers, 1984 (pp. 491-501).

\* cited by examiner

100

121

123

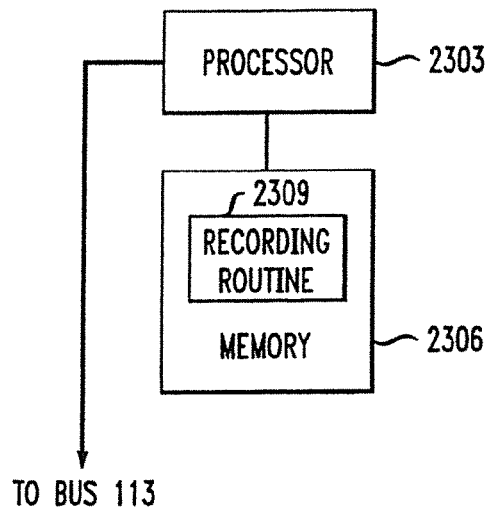
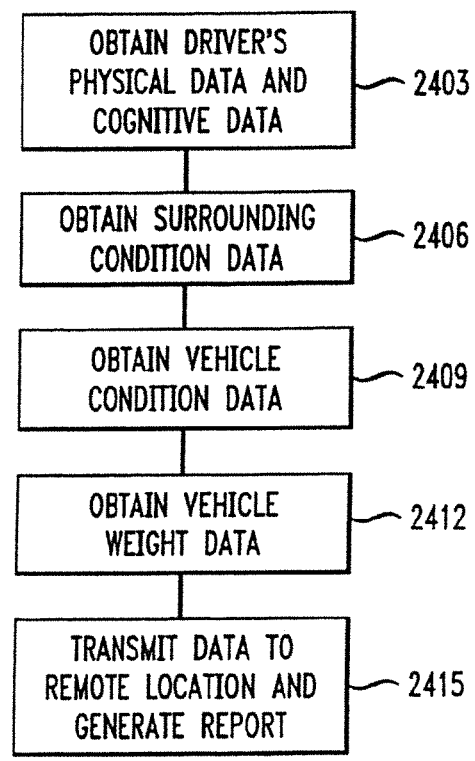

800

163

2214

TECHNIQUE FOR OPERATING A VEHICLE EFFECTIVELY AND SAFELY

CROSS-REFERENCE TO RELATED APPLICATION

The present application is a continuation of U.S. patent application Ser. No. 13/042,304, filed Mar. 7, 2011, which is a continuation of U.S. patent application Ser. No. 11/837,393, filed Aug. 10, 2007, now U.S. Pat. No. 7,902,969, which is a continuation of U.S. patent application Ser. No. 11/226,513 filed Sep. 13, 2005, now U.S. Pat. No. 7,417,531, which is a continuation application of U.S. patent application Ser. No. 10/380,449, filed Mar. 10, 2003, now U.S. Pat. No. 6,982,635, which claims the benefit of International Application No. PCT/US2001/029425 filed on Sep. 20, 2001, which was published under PCT Article 12(2) in English and which claims the benefit of (a) Provisional Application No. 60/234,134 filed on Sep. 21, 2000, and (b) Provisional Application No. 60/283,685 filed on Apr. 13, 2001. Each of these related applications are incorporated by reference herein.

FIELD OF THE INVENTION

The invention relates to systems and methods for operating a vehicle, and more particularly to a system and method for assisting vehicle users to operate a vehicle safely and effectively.

BACKGROUND OF THE INVENTION

Safety is always a major concern of vehicle drivers and passengers. The automobile industry developed well known devices such as adaptive cruise control, traction control, anti-lock braking, TRAXXAR stability control, rain sensors, backup/parking sensors and active suspension systems for incorporation in a vehicle to improve its safety. For example, a vehicle relies on the adaptive cruise control to adjust its speed to safely follow other vehicles in traffic. Specifically, it relies on radar or infrared sensors to measure the distance to the vehicle just ahead. If the vehicle ahead speeds up or slows down, an onboard computer adjusts the throttle or brakes to maintain a safe distance. The TRAXXAR stability control relies on use of sensors to measure the steering wheel position, and the yaw rate and lateral acceleration of the vehicle. These sensors work with the onboard computer to controllably apply brakes at selected wheels to avoid potential skids. With the advent of computer control technology, more and more vehicle safety devices are being developed which include, e.g., an active roll control (ARC) system controlling steering and suspension to prevent any vehicle rollover.

In addition, navigation systems based on global positioning system (GPS) technology were developed for use in a vehicle. One such navigation system is capable of receiving signals from a constellation of satellites, which are part of the GPS. Based on the received signals, such navigation system identifies the vehicle's location, e.g., in latitude and longitude. The navigation system also detects the vehicle's speed and direction. With geographic information stored in the on-board computer, the navigation system is capable of audio-visually communicating to a user instructions for reaching a given destination. Another navigation system is capable of receiving signals from ground based servers that function as an intermediary between a constellation of satellites and the vehicles equipped with a GPS system. Yet another navigation system utilizes cellular telephone sites and cross triangulation to locate vehicles equipped with appropriate systems. These vehicle navigation systems may be incorporated into a vehicle or may be realized in the form of a handset device, which can be "docked" inside the vehicle.

It is envisioned that in the near future the navigation systems will utilize realtime weather, traffic and road surface condition information to help drivers avoid areas having inclement weather, congested areas and undesirable roads. Such information, which may be provided using sensors in the road and cameras at intersections, is continuously fed to a central computer. Selected part of the collected information is then transmitted from the central computer to a receiver in a vehicle in a wireless manner.

Alternatively, each vehicle on the road may serve as a "moving sensor" collecting the weather, traffic and road condition information using radar and infrared sensors therein. The collected information is then transmitted from each vehicle to the central computer where it is processed and from where it is distributed to other vehicles for their utilization. Of course, the more vehicles that serve as the moving sensor, the more accurate and comprehensive the traffic and road condition information would be. There are a number of prior art systems for collecting weather, traffic, and road condition information, such as those described in U.S. Pat. Nos. 6,133,853 and 6,148,261.

With the above-described state-of-the-art vehicle devices and navigation systems, the realization of the ultimate vehicle which is capable of driving itself is just a matter of time.

SUMMARY OF THE INVENTION

To ensure the safety of a vehicle user, there are at least three sets of conditions which need to be observed. They include (a) the vehicle condition, (b) the surrounding conditions and (c) the driver condition. The vehicle condition concerns the functionalities built into the vehicle and the performance of such functionalities. The surrounding conditions concern the road, weather, traffic, etc., which the vehicle encounters. The driver condition concerns the physical condition and the cognitive state of the person who handles the vehicle. Safe driving is a function of all of these conditions. However, each condition does not have to be optimal to achieve safe driving. For example, an unfavorable surrounding condition may be compensated by both favorable vehicle condition and sound driver condition to achieve safe driving. A driver in an unsound condition may be compensated by favorable vehicle and surrounding conditions.

Thus, in accordance with an aspect of the invention, different tests are instituted in a vehicle control system to test the cognitive state of the user handling the vehicle. For example, these tests may require the user to correctly identify different colors presented in a random order, and/or identify himself/herself in a proper voice pattern before he/she can operate the vehicle. Such cognitive tests may be invoked by an unusual change in the user's body temperature relative to the ambient temperature, a relatively high carbon dioxide concentration in the vehicle compartment, and/or the user's erratic driving behavior.

In accordance with another aspect of the invention, the vehicle condition may be improved, e.g., by adjusting resistance of certain operating elements such as the steering wheel, gas pedal and brake pedal to prevent abrupt turns, and acceleration and braking of the vehicle. The amount of resistance imparted in the operating elements may be a function of the weight of the user. In addition, tire traction may be controlled effectively by adjusting their camber to change their coefficient of friction. Further, the condition of a tire as to whether it is properly inflated may be tested by comparing the temperatures of the sidewalls and that of the tread circumference of the tire. Still further, the safe distance maintained by a first vehicle from a second vehicle which the first vehicle, under the adaptive cruise control, follows is not a function of only the speed of the first vehicle as in prior art. Rather, it is a function of at least the speed and the weight of the first vehicle.

In accordance with yet another aspect of the invention, a control system in the vehicle detects and reacts to surrounding conditions such as presence of a water stream on a road surface. For example, before the vehicle crosses the water stream, the levelness of the road surface is measured by the control system, which may then adjust the tilting angle of the front wheels during the water stream crossing to increase the lateral stability of the vehicle.

In accordance with still yet another aspect of the invention, a driving program may be downloaded from a remote server, which demonstrates to the user how to handle an upcoming driving situation. The driving program is selected based on the surrounding conditions, e.g., weather, traffic and road conditions which make up the driving situation. As the vehicle approaches the supposed driving situation, the control system of the vehicle verifies whether the surrounding conditions remain virtually the same as before. In addition, the control system checks whether the driver condition and vehicle condition are favorable. If the driving situation is virtually unchanged and the driver and vehicle conditions are favorable, the control system controllably handles the driving situation in a manner similar to that demonstrated. Otherwise, the control system may cause the vehicle to deviate from the demonstrated way of handling the driving situation, e.g., by lowering its speed to ensure the safety of the user.

BRIEF DESCRIPTION OF THE DRAWING

Further aspects, features and advantages of the invention will become apparent from the following detailed description taken in conjunction with the accompanying drawing showing an illustrative embodiment of the invention, in which:

FIG. 4 is a block diagram of a recorder subsystem in the control system of FIG. 1;

FIG. 5 illustrates a flow chart depicting a process for recording data for use in a report in accordance with the invention;

DETAILED DESCRIPTION

The present invention is directed to a technique for assisting a vehicle user to operate a vehicle effectively and safely. To that end, auto manufacturers developed such systems as adaptive cruise control, traction control, anti-lock braking, TRAXXAR stability control, rain sensors, backup/parking sensors and active suspension systems for incorporation in vehicles.

Figure 1:
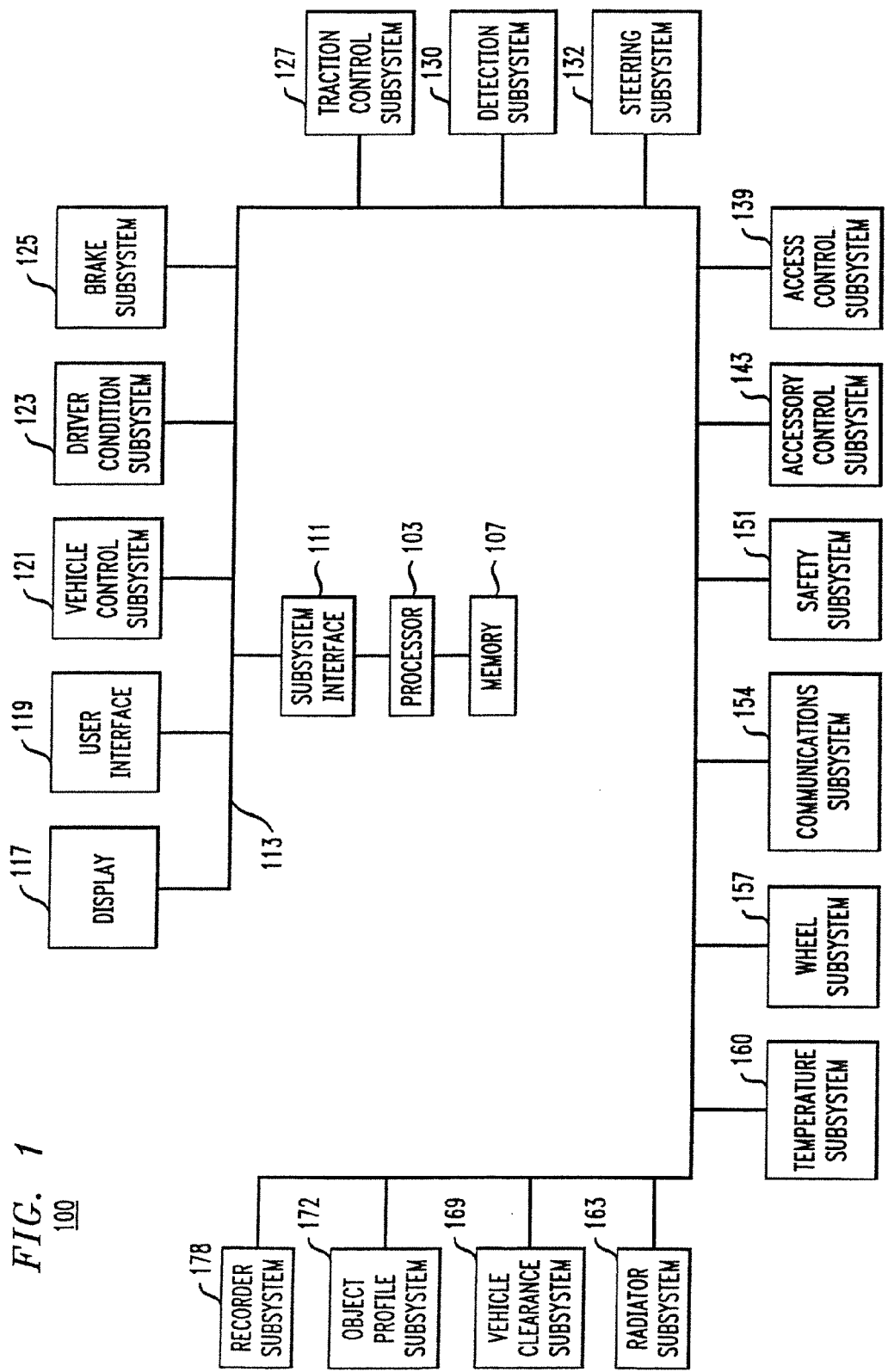
FIG. 1 is a block diagram of a control system for use in a vehicle in accordance with the invention.

FIG. 1 illustrates control system 100 embodying the principles of the invention for use in a vehicle. System 100 places previously unrelated vehicle subsystems under centralized control, thereby allowing data sharing among the subsystems effectively and coordinating their functions synergistically to realize safety features in accordance with the invention. In addition, system 100 provides a user with a user interface to interact with system 100, thereby assisting the user to operate the vehicle effectively and safely.

As shown in FIG. 1, central to system 100 is processor 103 of conventional design. Processor 103 is connected to memory 107 and subsystem interface 111. The latter is an ensemble of standard inputs/outputs (I/O's) connecting processor 103 to the subsystems to be described. Processor 103 performs various tasks in system 100 according to certain routines stored in memory 107. For example, through interface 111, processor 103 collects information from the subsystems for analysis, and transmits data and control signals to the subsystems.

Interface 111 connects the subsystems through common bus 113, which include display 117, user interface 119, vehicle control subsystem 121, driver condition subsystem 123, brake subsystem 125, traction control subsystem 127, detection subsystem 130, steering subsystem 132, access control subsystem 139, accessory control subsystem 143, safety subsystem 151, communications subsystem 154, wheel subsystem 157, temperature subsystem 160, radiator subsystem 163, vehicle clearance subsystem 169, object profile subsystem 172, and recorder subsystem 178.

By way of example, display 117 is a liquid crystal display (LCD) located on a dashboard of the vehicle. Display 117 includes a LCD driver (not shown) for processor 103 to control the display of text and graphics thereon in a predetermined format. User interface 119 comprises conventional audio circuitry including a microphone, voice recognition circuit, voice synthesizer and speaker to allow communications of verbal commands and audio information with system 100. User interface 119 may also comprise an indicator device, e.g., a mouse, touchpad, roller ball, or a combination thereof, which enables the user to move a cursor on display 117 and to, e.g., point and click at a displayed option or icon to select same. In addition, interface 119 may incorporate well-known touch-screen circuitry (not shown). With this circuitry, the user can interact with processor 103, e.g., using a finger or a stylus to touch the surface of display 117, which is tactile-sensitive. Processor 103 receives from the touch screen circuitry a signal identifying the location on display 117 where it has been touched. If such a location matches the predetermined location of one of displayed options or icons, processor 103 determines that the option or icon has been selected. Otherwise, a cursor is placed at the touched location on display 117, prompting for an input from the user.

In addition, processor 103 may be programmed to interface with various biometric devices, such as handwriting, fingerprint, and retina recognition systems. Processor 103 may be programmed to recognize handwritten characters, and may receive through the touch-screen circuitry images of characters drawn by the user on display 117. Any recognized characters corresponding to the drawn images then become the user input.

Figure 2:
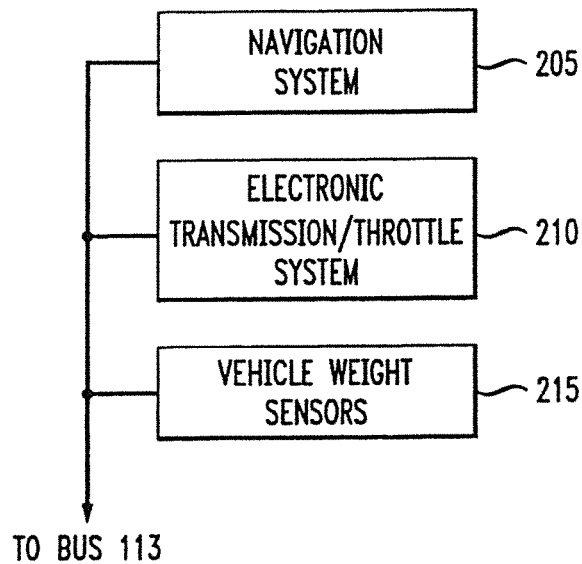
FIG. 2 is a block diagram of an vehicle control subsystem in the control system of FIG. 1.

Vehicle control subsystem 121 includes navigation system 205 in FIG. 2, which provides onboard and/or on-line navigation capability. In a well-known manner, system 205 receives signals from a constellation of satellites which is part of the global positioning system (GPS). In response to these signals, system 205 pinpoints the vehicle's location in latitude and longitude. Alternatively, the vehicle's location may be determined by other well known methodologies such as triangulation based on signals from global system for mobile communications (GSM) servers. In addition, system 205 receives the vehicle directional and speed information from a compass subsystem (not shown) and an accelerometer (not shown) in the vehicle, respectively.

When the user utilizes navigation system 205 to request instructions for a given destination, the user is elicited for information concerning the destination, any intermediate stops, etc. Such elicitation is realized by posing questions on display 117 and/or by uttering those questions using a synthesized voice through the speaker in user interface 119. The user then provides verbal responses (or commands) to such questions through the microphone in same. Relying on the aforementioned speech recognition circuitry, navigation system 205 recognizes and registers the responses. Using stored map information, system 205 then provides on display 117 a suggested route leading to the destination. Furthermore, based on the knowledge of the vehicle's instantaneous speeds and directions, system 205 is capable of verbally and visually directing the user to the destination.

Because of the limited capacity of the storage for the map information or because the map information needs to be updated from time to time, it will be appreciated that system 205 would instead obtain the necessary, latest map information from an on-line service through a cellular or wireless connection. One such technique for downloading map information is described, e.g., in International Pub. WO 98/59215 published on Dec. 30, 1998.

To ensure the safety of a vehicle user, there are at least three sets of conditions that need to be observed. They include (a) the vehicle condition, (b) the surrounding conditions and (c) the driver condition. The vehicle condition concerns the functionalities built into the vehicle and the performance of such functionalities. The surrounding conditions concern the road, weather, traffic, etc. which the vehicle encounters. The driver condition concerns the physical condition and the cognitive state of the person who handles the vehicle. Safe driving is a function of all of these conditions. However, each condition does not have to be optimal to achieve safe driving. For example, an unfavorable surrounding condition may be compensated by both favorable vehicle condition and sound driver condition to achieve safe driving. A driver in an unsound condition may be compensated by favorable vehicle and surrounding conditions.

Figure 3:
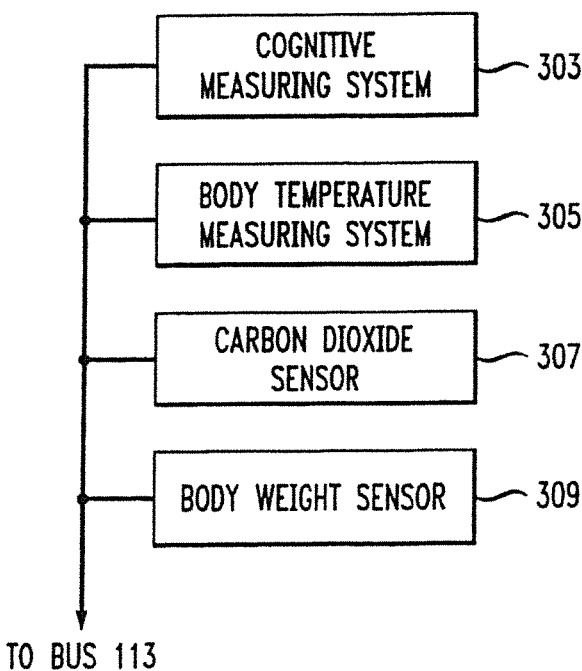
FIG. 3 is a block diagram of a driver condition subsystem in the control system of FIG. 1.

Thus, in accordance with an aspect of the invention, system 100 includes driver condition subsystem 123 to provide information concerning the physical condition and cognitive state of the user handling the vehicle. Referring to FIG. 3, subsystem 123 comprises cognitive measuring system 303 for measuring the user's alertness, which may be adversely affected by illness, extreme fatigue, abnormal stress, medication or alcohol. For example, to determine whether the user is alert enough to drive, when the user attempts to start the subject vehicle, system 303 causes different colors in random order to be shown one by one on display 117. The user is requested to identify each displayed color via voice recognition or selection of an appropriate choice shown on display 117. If each displayed color is correctly identified, processor 103 causes the vehicle to start.

Alternatively, each potential user of the vehicle is required to record his/her name utterance beforehand, and the voice pattern in terms of the composition of the frequency components of such an utterance is stored in memory 107. As a cognitive test, system 303 may request via audio media the user to utter his/her name after the user attempts to start the vehicle. Even if the user can produce his/her name, the produced voice pattern may deviate from the normal voice pattern because of his/her physically unfit or cognitively unsound state. Thus, processor 103 then compares the voice pattern of the current name utterance with that of each name utterance previously stored. If processor 103 determines that the voice pattern of the current name utterance substantially matches that of one of the name utterances previously stored, processor 103 causes the vehicle to start.

Referring to FIG. 4, recorder subsystem 178 is provided for recording data related to the driver's condition and behavior, the vehicle's condition, and the surrounding conditions. The data is used in a report that illustrates elements of the trip in the context of the driver's physical condition and cognitive state, vehicle condition and behavior, and conditions of the road and weather. Recorder subsystem 178 utilizes data accumulated by various subsystems in system 100, such as driver condition subsystem 123, communications subsystem 154, and vehicle control subsystem 121. As shown in FIG. 4, recorder subsystem 178 includes processor 2303 and memory 2306, and recording routine 2309 stored therein. Instructed by recording routine 2309, processor 2303 accesses and retrieves data from the various subsystems and store the data in memory 2306. Processor 2303 may communicate the data to a remote location, via communications subsystem 154. The remote location receives the data from which information is derived for use in reports for fleet management, police, insurance, and/or other purposes.

Referring to FIG. 5, in accordance with recording routine 2309, processor 2303 at step 2403 obtains from driver condition subsystem 123 data representing the driver's physical condition and cognitive state. Specifically, through bus 113, processor 2303 accesses driver condition subsystem 123 for data representing the driver's body temperature, blood pressure, alertness, etc. Processor 2303 stores the data in memory 2306 in association with time t.

At step 2406 processor 2303 obtains surrounding condition data including weather condition data, road condition data and traffic condition data from detection subsystem 130, communications subsystem 154, etc. The surrounding condition data is stored in memory 2306 in association with time t as well. At step 2409 processor 2303 obtains data representing the vehicle's condition, e.g., the vehicle's instantaneous speed, direction and acceleration from vehicle control subsystem 121. The vehicle condition data is similarly stored in memory 2306 in association with time t.

At step 2412 processor 2303 obtains vehicle weight data from vehicle control subsystem 121 incorporating vehicle weight sensors 215 in FIG. 2. Weight sensors 215 are placed at selected points of the vehicle axles on which the body of the vehicle sits. Such vehicle weight data is also stored in memory 2306 in association with time t. As such, data can be retrieved from memory 2306 and analyzed individually or in combination with respect to specific times or periods. For example, with the vehicle weight data, any weight shift of the vehicle can be identified and analyzed with respect to specific times or periods. It should be realized that additional data can be analyzed when determining the context of the driver's situation at time t. For example, navigation data from vehicle control subsystem 121 can be used to determine the vehicle's location at time t and indicate whether the driver was on course at that time.

In addition, recorder subsystem 178 may include a driver score routine for converting and organizing collected data in a predetermined format for the driver to review during and after a trip. For example, instructed by the driver score routine, processor 2303 retrieves selected data in memory 2306 which, e.g., includes the driver cognitive data, driver physical condition data, weather condition data, road condition data, and vehicle speed, direction and acceleration data. Based on the selected data, processor 2303 generates statistics for a selected time t or period in a driver score card form for evaluating the previous driving experience. Thus, when the score card or report is generated, the driver condition data may be evaluated synchronously with the weather condition data and/or the vehicle condition data.

In this instance, processor 2303 at step 2415 transmits some or all of the data stored in memory 2306 to a remote location through communications subsystem 154. The remote location, receptive to the transmission, may be at a vehicle dispatch office for a transportation company. At the remote location, a computer system processes the data received from multiple vehicles to generate various reports. These reports may include, e.g., information regarding whether the driver's reaction to a particular event was influenced by the vehicle, driver and/or surrounding conditions.

The aforementioned cognitive test may be triggered from time to time while a user is driving. For example, it may be triggered by an unusual rise of the body temperature of the user. To that end, subsystem 123 also includes body temperature measuring system 305, which utilizes a first thermo-sensor for measuring the user's body temperature by contact, e.g., by incorporating the thermo-sensor in the user's seat in the vehicle. Alternatively, an infrared sensitive thermo-sensor may be used, instead, which is placed close to the user, and which measures the user's body temperature based on the heat radiated from his/her body. A thermo-sensor may also be placed in the grip of the steering wheel for sensing the body temperature of the user. System 305 utilizes a second thermo-sensor to measure the ambient temperature in the vehicle compartment. Processor 103 takes the readings from the second thermo-sensor, after the ambient temperature becomes steady, i.e., it is within a predetermined range over time, which is readily achieved in an air-conditioned vehicle where the thermostat is set at a particular temperature. When the ambient temperature is in a steady state, processor 103 takes readings from the first thermo-sensor from time to time, if the user's body temperature goes up beyond a predetermined threshold, indicating his/her growing fatigue or physical unsoundness. The above-described cognitive test is triggered, if the user fails the above cognitive test, or does not respond, processor 103 causes braking using brake subsystem 125 to slow the vehicle down. At the same time, it causes steering subsystem 132, guided by navigation system 205 and radar and/or infrared sensors in detection subsystem 130 (described below), to steer the vehicle onto the shoulder of a road.

The cognitive test may also be triggered by detection of a high level of a concentration of carbon dioxide in the vehicle compartment, which causes yawning and sleepy condition. As soon as carbon dioxide sensor 307 in the vehicle compartment detects the level of the carbon dioxide concentration exceeds a predetermined level, processor 103 causes the windows of the vehicle to be opened to let fresh air in, and then invokes the cognitive test.

In addition, the cognitive test may be triggered by any erratic driving behavior. Processor 103 determines such a behavior by measuring the vehicle acceleration and deceleration pattern, the frequency and abruptness of the accelerations and decelerations. If they are frequent and abrupt, processor 103 determines that the user is having an erratic driving behavior, and thus triggers the above cognitive test. At the same time, processor 103 may adjust the resistance of the accelerator in the vehicle in a manner described below to discourage the user from speeding, and may also generate an exception report recording the erratic driving incident. Such a report may be stored in memory 107 for further investigation.

A second way of determining any erratic driving behavior is straight line tracking. Detection subsystem 130 includes radar, sonar, infrared sensors, Doppler radar, magnetometers, CCD cameras, and/or other object finder mechanisms, and is used for, among other things, monitoring the road condition and objects ahead. Processor 103 determines that a road section ahead is relatively straight if subsystem 130 detects that two or more vehicles in that road section has virtually no lateral movement toward one another. Alternatively, where the lane boundaries are detectable, for example, magnets being buried along lane boundaries whose magnetic field is detectable by the magnetometer in subsystem 130, processor 103 can readily determine whether such boundaries define a straight road section ahead. When processor 103 determines a straight road section ahead, processor 103 polls steering subsystem 132 for signals indicating any abnormal or excessive steering on the part of the user when the subject vehicle is traversing the straight road section, which requires holding the steering wheel steady. If the received signals indicate any excessive steering, processor 103 determines that the user is having an erratic driving behavior and thus triggers the above cognitive test.

Where street lines are available and visible, using the CCD camera, detection subsystem 130 captures images of the lines. Processor 103 converts the images to points and determines the parameters of the road configuration and "vehicle attitude."

Figure 6:
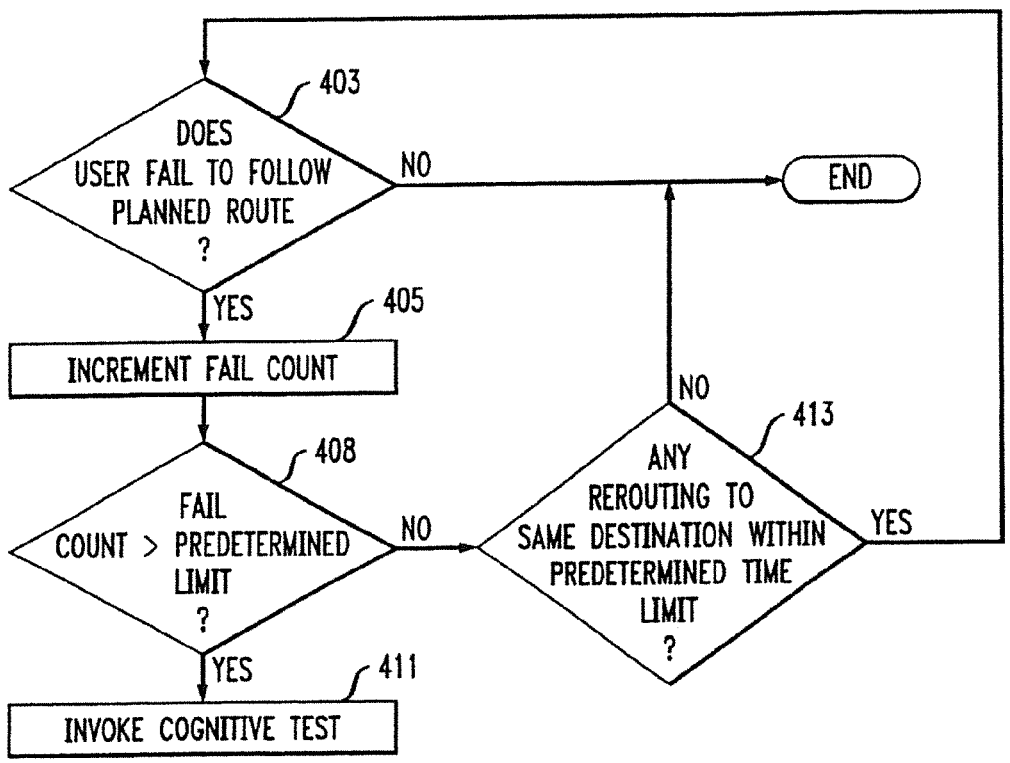
FIG. 6 is a flow chart depicting a process for invoking any cognitive test in accordance with the invention.

A third way of determining an erratic driving behavior is whether the user repeatedly gets lost, and misses any supposed turns or freeway exits. For example, the user may use navigation system 205 to plan a route to a destination. In that case, instructed by a routine stored in memory 107, processor 103 determines whether the user fails to follow a planned route under the guidance of navigation system 205, as indicated at step 403 in FIG. 6. If the user manages to follow the planned route, this routine comes to an end. Otherwise, if the user fails to follow the planned route, processor 103 at step 405 increments a FAIL COUNT which keeps track of any such failure. This FAIL COUNT is initially set at zero. At step 408, processor 103 determines whether the FAIL COUNT is greater than a predetermined limit. For example, the predetermined limit in this instance is three. If the FAIL COUNT exceeds the predetermined limit, processor 103 at step 411 invokes the above-described cognitive test to check whether the user is fit to drive. Otherwise, the routine proceeds to step 413 described below. In accordance with an aspect of the invention, if the user uses navigation system 205 to reroute to the same destination after his failure to follow the previous planned route, navigation system 205 signals processor 103 to notify the latter of such rerouting. Thus, at step 413 processor 103 determines whether any signal indicating rerouting to the same destination is received from navigation system 205 within a predetermined time limit. If no such signal is received within the time limit, the routine again comes to an end. Otherwise, the routine returns to step 403 described above.

In addition, driver condition subsystem 123 also includes body weight sensor 309 in FIG. 3 for measuring the weight of the user. Sensor 309, which is incorporated in the user's seat, measures the weight of the user while sitting on the seat. The user's weight varies with the force he/she applies to operate vehicle equipment. For instance, the heavier the user is, the stronger force he/she is likely to apply onto the gas and brake pedals, resulting in abrupt accelerations and decelerations. To ensure effective and smooth operation of the vehicle, in accordance with another aspect of the invention, certain vehicle equipment operable by the user has its resistance against force made adjustable according to the user's weight. To that end, for each force resistance adjustable equipment (e.g., the gas pedal, brake pedal and steering wheel in this instance), a look-up table is stored in memory 107, which associates user's weights with different extents of resistance, respectively. In general, the heavier the user, the more resistance is accorded to the equipment. Thus, in response to a signal from sensor 309, indicating the user's weight, processor 103 consults the look-up table to prescribe and impart the proper resistance to the gas and brake pedals to prevent unnecessary abrupt accelerations and decelerations of the vehicle, and to the steering wheel to facilitate smooth turns. Of course, the automatic equipment resistance adjustment is subject to an override by the user.

In an alternative embodiment, driver condition subsystem 123 may include a feedback system (not shown) associated with the steering wheel, foot pedals, and gear shift for determining and setting optimal resistance for the particular driver and the particular driving condition. The feedback system measures the body strength of the driver in reference to foot pedal use, steering, and gear shifting. Because in this embodiment it is assumed that body weight is not a good indicator of strength, the feedback system can be used to distinguish between a heavy, weak person and a light, strong person. The feedback system may include electro-mechanical transducers and resistance mechanisms coupled to the foot pedals, steering wheel and gear shift. Before the user begins a trip, he/she presses on each of the foot pedals. The feedback system applies resistance to the foot pedals while the driver presses the pedals. A point of equilibrium is reached between the pressure applied by the driver's foot and the foot pedals, as controlled by the feedback system. The resistance applied to the foot pedals by the feedback system at the point of equilibrium, is the resistance that the feedback system applies to the foot pedals during vehicle operation. A similar process may be used to determine the resistance that the feedback system applies to the steering wheel and gear shift during operation of the vehicle.

The feedback system may also monitor the driver's strength during the operation of the vehicle. During operation of the vehicle the feedback system may measure deviations form the equilibrium point established before the driver began the trip and may adjust the resistance of the foot pedals, steering wheel, or gear shift. A change in user strength may be caused, for example, by driver sudden illness or fatigue.

The feedback system may also adjust the resistance of the controls in response to information from driver condition subsystem 123, which indicates that the driver has become ill or fatigued and may not be able to apply enough force to the foot pedals, steering wheel, or gear shift in response to certain driving conditions. The feedback system may also automatically re-adjust the resistance applied to the steering wheel, foot pedals, and gear shift during various weather, road and traffic conditions. In response to the collected surrounding condition data, the feedback system may adjust the resistance on one or more of the foot pedals, steering wheel, or gear shift. For example, if the road condition data or weather data indicate that there is snow on the road, the feedback system may increase the resistance of the steering wheel, to allow for steady steering.

Adjustable length and angle pedals, steering column, and gear shift are included in the vehicle to assist in providing optimal comfort and resistance for the driver. By adjusting the length or angles of these controls, the user's comfort may increase, but the amount of force the user is capable of applying to the control may change. For example, a foot pedal that is located farther away from the user may be comfortable for the user, but may require the user to extend his/her leg further when applying pressure on the foot pedal. In this situation the user may be putting less pressure on the foot pedal than if the foot pedal is closer to the user. Driver condition subsystem 123 takes into account the location of the controls when determining resistance settings.

Referring back to FIG. 2, vehicle control subsystem 121 includes electronic transmission/throttle system 210, which operates under the control of processor 103 in accordance with certain drivetrain routines. The program instructions defining these routines are stored in memory 107 in this instance. Alternatively, they may be stored in a memory (not shown) in subsystem 121. The drivetrain routines enable system 210 to help the user to handle different road conditions, in cooperation with other subsystems such as aforementioned detection subsystem 130 and steering subsystem 132, traction control subsystem 127, wheel subsystem 157, etc.

Figure 7:
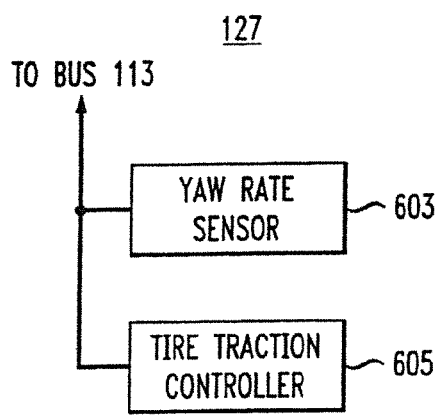
FIG. 7 is a block diagram of a traction control subsystem in the control system of FIG. 1.

As shown in FIG. 7, traction control subsystem 127 includes yaw rate sensor. 603 for measuring any lateral acceleration of the vehicle, and tire traction controller 605 for controlling the tire traction or "grip" on the road to maintain vehicle stability. Tire traction is important especially during the vehicle's cornering which causes weight transfer on the tires and instability. Subsystem 127 may manipulate the camber of each tire to adjust the coefficient of friction (CF) of the tire to achieve the vehicle stability. The CF of a tire may be expressed as a ratio of the traction or friction afforded by the tire to the force exerted on the road through the contact patch of the tire, i.e., tire footprint contacting the road. A higher CF provides greater traction while a lower CF provides less. An increase in the lateral stability is indicated by a decrease in the yaw rate measured by sensor 603.

As is well known, the camber describes the tilt of the tire, measured as the angle between the vertical and a plane through the tire's circumference. When a tire is standing perpendicular to the road. It is said to have zero camber. If the top of the tire tilts toward the vehicle, it is said to have negative camber. Otherwise, if the top of the tire tilts away from the vehicle, it is said to have positive camber.

Processor 103 may cause controller 605 to change the camber of the tires to adjust the tires' CF level, and thus their traction. For example, in response to a request by processor 103 for increasing the traction, controller 605 operates wheel subsystem 157 to tilt the tires controlled thereby to obtain negative camber, and thus a higher CF level, to deliver greater traction. In addition, the air pressure of a tire and its aspect ratio the ratio of the height of the sidewall of the tire to the width of the tread thereof—affects the traction as well.

Figure 8:
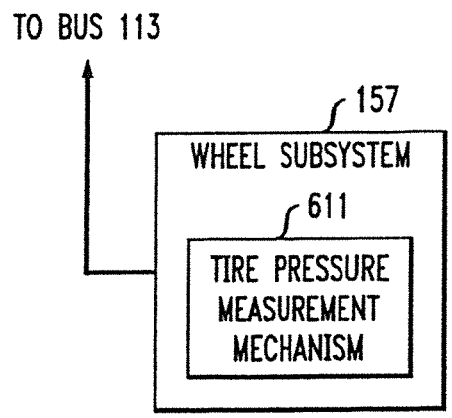
FIG. 8 is a block diagram of a wheel subsystem in the control system of FIG. 1.
Figure 9:
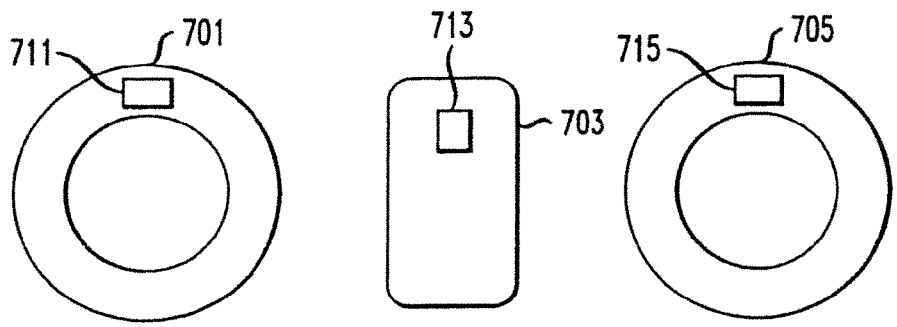
FIG. 9 illustrates placements of pyrometers in a tire in accordance with the invention.

Wheel subsystem 157 in FIG. 8 includes tire pressure measurement mechanism 611 for monitoring, among others, the air pressure of each tire. Too high a tire pressure causes a harsh vehicle ride and poor tire traction. On the other hand, too low a tire pressure causes premature wear of the tire, bad fuel economy and poor handling of the vehicle. In monitoring the tire pressure, mechanism 611 uses pyrometers therein to measure the temperatures of different sections of each tire. One such tire is illustrated in FIG. 9, where the left sidewall of the tire is denoted 701; the tread circumference thereof is denoted 703; and the right sidewall thereof is denoted 705. Pyrometers 711, 713 and 715 are incorporated in, or alternatively attached to, the inside of left side-wall 701, tread circumference 703, and right sidewall 705, respectively, thereby avoiding direct contact by the pyrometers with the road surface. Specifically, pyrometer 713 is placed in the middle of tread circumference 703.

Figure 10:
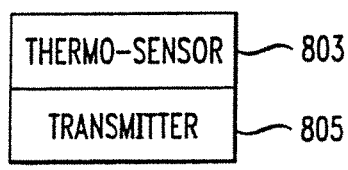
FIG. 10 illustrates the components of a pyrometer in accordance with the invention.

FIG. 10 illustrates one such pyrometer used, generically denoted 800. As shown in FIG. 10, pyrometer 800 includes thermo-sensor 803 for measuring the temperature of the tire, and transmitter 805 for transmitting the signal indicating the measured temperature received from thermo-sensor 803. The transmitted signal is receptive by wheel subsystem 157 where the measured temperature is recovered based on the received signal. With the above arrangement, subsystem 157 is capable of obtaining the temperatures of the left section, mid-section and right section of each tire. Since the vehicle has four tires, twelve pyrometers are used in this instance, and their locations are recognized by subsystem 157. In addition, the transmitted signal from each pyrometer also contains information identifying the pyrometer from which the transmitted signal is originated, and thus the location of the pyrometer, i.e., the tire and its section that the pyrometer is on.

Figure 11:
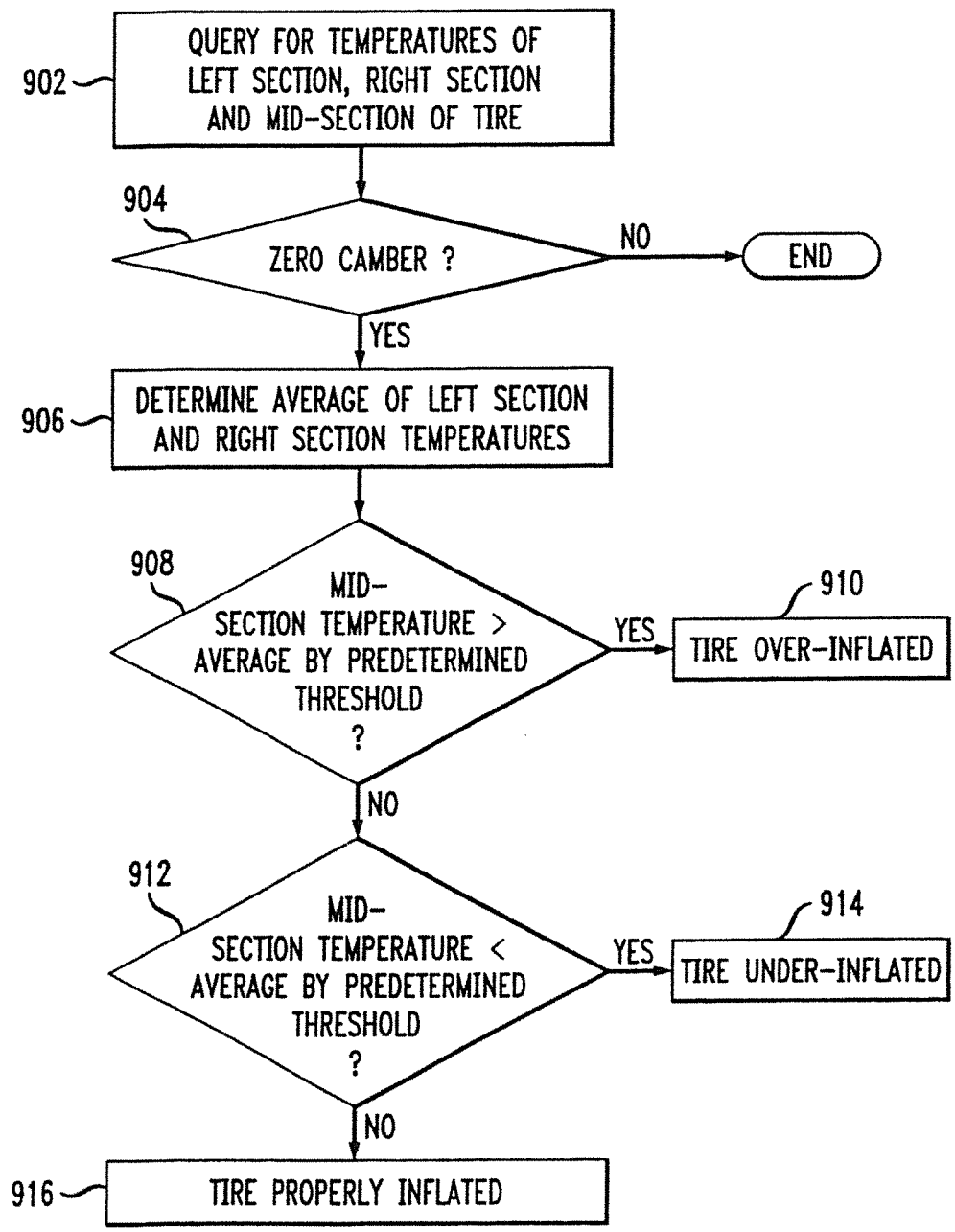
FIG. 11 is a flow chart depicting a process for determining whether a tire is properly inflated in accordance with the invention.

To determine whether a tire is properly inflated while the user is driving the vehicle, the tire needs to be set at zero camber and run on a road for at least a predetermined distance. Processor 103 then queries wheel subsystem 157 for the temperatures of the left section, mid-section, and right section of the tire, as indicated at step 902 in a routine shown in FIG. 11. Processor 103 at step 904 verifies the zero camber setting by comparing the left section temperature with the right section temperature. The zero camber setting is considered negative when the left and right section temperatures differ from each other by more than a first predetermined threshold, and the subject routine comes to an end. Otherwise, processor 103 at step 906 determines the average of the left section temperature and the right section temperature. Processor 103 compares the resulting average temperature with the mid-section temperature. Processor 103 at step 908 determines whether the mid-section temperature is higher than the average temperature by a second predetermined threshold. If so, processor 103 determines that the tire is over-inflated, as indicated at step 910, and issues a warning on display 117 about the over-inflation of the tire. Otherwise, processor 103 at step 912 determines whether the mid-section temperature is lower than the average temperature by the second predetermined threshold. If so, processor 103 determines that the tire is under-inflated, and issues a warning on display 117 about the under-inflation of the tire, as indicated at step 914. Otherwise, if processor 103 determines that the mid-section temperature is neither higher than the average temperature by the second predetermined threshold nor lower than the average temperature by the third predetermined threshold, processor 103 determines that the tire is properly inflated, as indicated at step 916.

Vehicle control subsystem 121 includes vehicle weight sensors 215 in FIG. 2 for measuring the weight of the vehicle body. Weight sensors 215 are placed at selected points of the vehicle axles on which the body of the vehicle sits, with its full weight conducting through the weight sensors onto the tires.

Instructed by one of the drivetrain routines which concerns adaptive cruise control of the vehicle, processor 103 causes electronic transmission/throttle system 210 and brake subsystem 125 to adjust the subject vehicle's speed to keep a safe distance from a second vehicle just ahead. It also relies on radar or infrared sensors in detection subsystem 130 to measure the distance to the second vehicle. If the second vehicle ahead speeds up or slows down, processor 103 adjusts the throttle or brakes of the subject vehicle to maintain the safe distance. In prior art, the safe distance is determined based on the current speed of the subject vehicle. However, in accordance with the invention, the safe distance is determined based not only on the current vehicle speed but also the weight of the vehicle. In other words, for a given vehicle speed, the amount of safe distance also varies with the weight of the vehicle. Specifically, for a given vehicle speed, the heavier the vehicle, the greater the safe distance is. In this illustrative embodiment, the safe distance is a function of the product of the current vehicle speed and the weight of the vehicle, measured by vehicle weight sensors 215.

It should be noted that the weight of the vehicle is not constant, which depends on the number of passengers in the vehicle and their actual weights, and whether it carries any cargo, e.g., in the trunk. The weight of the vehicle also includes the weight of any trailer towed by the vehicle, also known as the "tongue weight." To that end, one or more tongue weight sensors (not shown) are placed on an axle(s) supporting the tongue weight. Processor 103 obtains the tongue weight value and adds it to the weight sensed by the vehicle weight sensors to obtain the total weight of the vehicle. It should also be noted that when a trailer is used, additional trailer brakes may be installed when the load and gear of the trailer exceeds a certain weight, e.g., 1,500 lbs. The trailer brakes which may be incorporated in brake subsystem 125 may be (1) electric, manual or automatic, or (2) hydraulic where the trailer brakes are applied according to the pressure on the brake pedal in the vehicle, or (3) conventional surge brakes, which use a master cylinder at the junction of the hitch and trailer tongue.

In accordance with another aspect of the invention, system 100 monitors changes in the vehicle weight distribution and compensates for such changes, while notifying the user of safety related problems. Such changes in vehicle weight distribution, for example those caused by weather conditions, may create erratic performance of the vehicle.

As mentioned above, weight sensors 215 are placed at selected points of the vehicle axles on which the body of the vehicle sits. The positions of sensors 215 represent measurement points, wherein the measurement points represent various locations on the vehicle where weight is measured. If for some reason the weight of the vehicle or its payload changes or shifts, weight sensors 215 detect the changes or shift in weight. Once a significant change or shift in weight is detected, processor 103 notifies the user of a possible safety problem, and interacts with traction control subsystem 127 to alleviate the problem.

Referring back to FIG. 7, yaw rate sensor 603 is used to measure any lateral acceleration of the vehicle, and tire traction controller 605 is used to control the tire traction or "grip" on the road to maintain vehicle stability. Tire traction is important especially during the vehicle's cornering which causes weight transfer on the tires and instability. This becomes more important when the vehicle is carrying payload near the maximum allowed weight. As weight shifts, controller 605 manipulates the camber of each tire to adjust the CF of the tire to achieve vehicle stability. Weight shifting may be caused by physical forces in cornering of a vehicle, or by a payload inadvertently shifting during transportation. Such a payload may be, for example, luggage on the roof or inside the trunk of the vehicle, or goods in the payload area of a truck.

In response to vehicle weight sensors 215 detecting a shift in payload, or yaw rate sensor 603 detecting lateral acceleration caused by a shift in payload, processor 103 causes controller 605 to change the camber of the tires to adjust the tires' CF level and thus, their traction.

The individual weight measures from weight sensors 215 can be used to realize a weight profile or weight distribution of the vehicle. To that end, processor 103 determines the average weight of the vehicle by adding all of the weight measures and dividing the sum by the number of sensors or measuring points. Processor 103 then compares the average weight with individual weight measures, respectively, to determine any weight imbalances at the corresponding measuring points.

Figure 12:
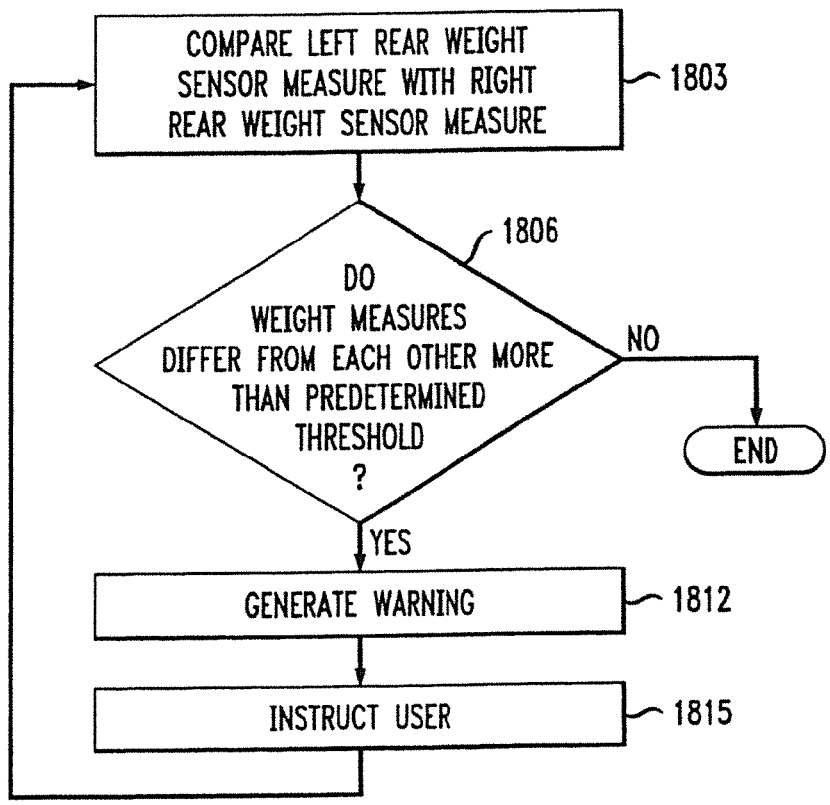
FIG. 12 is a flow chart depicting a load balance routine in accordance with the invention.

Referring to FIG. 12, which illustrates a load balance routine. Instructed by such a routine, processor 103 at step 1803 compares the weight measure by a weight sensor located on the right rear of the vehicle to that by another sensor located at the left rear of the vehicle. Processor 103 at step 1806 determines whether the weight measures differ from each other by more than a predetermined threshold. Such a threshold is pre-selected to ensure the weight distribution in the rear of the vehicle is within a safe operating range. If it is determined that the difference between the measures is less than or equal to the predetermined threshold, the routine comes to an end. Otherwise, processor 103 at step 1812 generates a warning, alerting the vehicle user about the weight imbalance. In addition, having determined the weight distribution of the vehicle, processor 103 at step 1815 instructs the user how to correct the imbalance. For example, processor 103 may provide such instructions as "Please Redistribute the Weight in the Rear of the Vehicle to the Left to Correct the Imbalance". While the user is redistributing the payload, processor 103 continues to update the weight distribution and advise the user as to whether the shifting of the payload has corrected the safety problem. If, for example, the user cannot correct the problem, processor 103 may then provide driving instructions to help the user handle the unbalanced vehicle. A similar process is used to determine whether the vehicle is balanced with respect to the front of the vehicle.

As mentioned above, during acceleration, braking, and cornering, the weight of the vehicle and its payload transfers. For example, in a turn, the weight transfers to the wheels on the outside of the turn, thereby imparting to the "outside wheels" the most traction. In a left turn the right side wheels are considered to be the outside wheels while in a right turn the left side wheels are considered to be the outside wheels. Because of the weight transfer, the payload may be displaced, resulting in a weight imbalance. To improve the vehicle traction after a turn causing such a weight imbalance, processor 103 may interact with traction control subsystem 127 in a manner described before and causes wheel subsystem 157 to adjust the camber of each tire, thereby changing the CF of the tire to achieve vehicle stability for unbalanced vehicle driving conditions.

Figure 13:
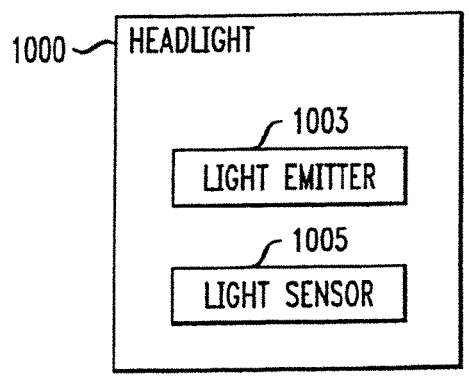
FIG. 13 illustrates the components of a fog lamp in accordance with the invention.

In accordance with another aspect of the invention, the speed of the vehicle for the adaptive cruise control may be adjusted as a function of visibility, i.e., the farthest distance which the user can see without difficulties. Specifically, the lower the visibility is, the lower the speed to which the vehicle is adjusted. Typically, the visibility is adversely affected by foggy, rainy or snowy weather condition. In that case, headlights in accessory control subsystem 143 are usually turned on to increase visibility. Referring to FIG. 13, each headlight used in this illustrative embodiment, generically denoted 1000, includes not only light emitter 1003 as in prior art, but also light sensor 1005 for helping measure the visibility. Using the fog, rain or snow as a light reflector, light sensor 1005 senses the amount of light from light emitter 1003 which is reflected by the fog, rain or snow back to sensor 1005. The thicker the fog, or the heavier the rain or snow, and thus the less the visibility, the more of the emitted light is reflected and sensed by sensor 1005. Since sensor 1005 is used to measure the reflected part of the emitted light, to reduce interference by the emitted light directly from emitter 1003, light sensor 1005 is surrounded by a shade shielding sensor 1005 from such direct interference. In addition, to reduce interference by the ambient light, sensor 1005 may be made sensitive to only selected light frequencies also emitted by light emitter 1003, which do not normally appear in the ambient light and are thus used to identify emitter 1003. The amount of the reflected light sensed by sensor 1005 is communicated to processor 103. The latter then adjusts the current speed of the vehicle, which varies with the amount of the reflected light sensed.

It should be noted that the visibility measurement in the subject vehicle may be broadcast to other nearby vehicles using communications subsystem 154 (described below) so that they can benefit from such a measurement. Indeed, the user of the subject vehicle may be a beneficiary of such visibility information received from another vehicle traveling in the same local area. The received visibility information may help processor 103 to obtain a more accurate visibility measurement by sensor 1005. Alternatively, the visibility information may be received from another source such as a central computer described below.

The subject vehicle may sometimes encounter water, e.g., rain water, flowing water or even deep water, while it is in operation. An accumulation of water on the road leads to a condition known as "hydroplaning" where the amount of the accumulated water exceeds the tires' ability to channel it out of the way. To detect, and assess the depth of water encountered by the vehicle, a humidifier and sonar are used in detection subsystem 130. Processor 103 adjusts the speed of the vehicle based on the water depth detected to control the amount of water the tires need to channel.

Figure 14:
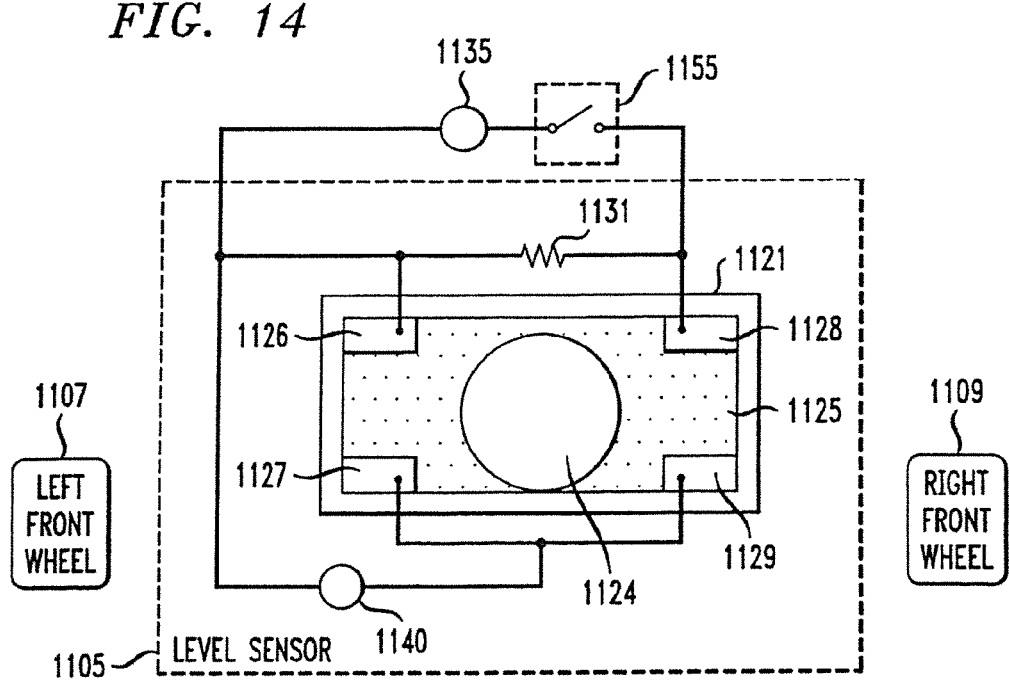
FIG. 14 illustrates an arrangement including a level sensor in accordance with the invention.

In accordance with another aspect of the invention, subsystem 130 also incorporates a level sensor, e.g., level sensor 1105 in FIG. 14, which is installed horizontally across an axle between left front wheel 1107 and right front wheel 1109 to detect any unlevelness of the road surface. As shown in FIG. 14, level sensor 1105 includes linear chamber 1121 wherein mercury drop 1124 is free to roll from one end of chamber 1121 to the other end thereof, although its movement is dampened by dampening fluid 1125 also in chamber 1121. Chamber 1121 is made of non-conductive material. However, when mercury drop 1124 rolls toward the left end of chamber 1121 because the road surface declines from right to left, it comes into contact with metallic terminal 1126 attached to the top portion of chamber 1121 and with metallic terminal 1127 attached to the bottom portion thereof. When mercury drop 1124 rolls toward the right end of chamber 1121 because the road declines from left to right, it comes into contact with metallic terminal 1128 attached to the top portion of chamber 1121 and with metallic terminal 1129 attached to the bottom portion thereof. Resistor 1131 having a predetermined electrical resistance value is connected between terminals 1126 and 1128. Voltage source 1135 is connected to terminal 1126 at one end thereof; and to terminal 1128 through switch 1155 at the other end thereof. Source 1135 which may be furnished by a battery in the subject vehicle provides a constant voltage V. Switch 1155 may be part of the ignition system, which is closed only after the vehicle is started. Voltage meter 1140 is connected to terminals 1127 and 1129 at one end thereof; and to terminal 1126 at the other end thereof. It should be realized that the level sensor used in this embodiment is for illustrative purposes.

Figure 15A:
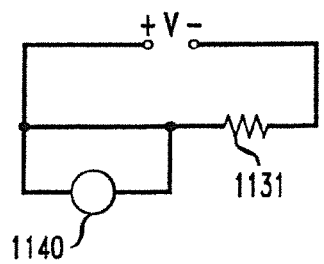
FIG. 15A illustrates a first equivalent circuit to the level sensor in FIG. 14.
Figure 15B:
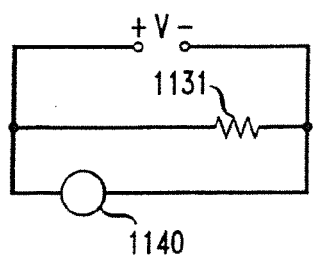
FIG. 15B illustrates a second equivalent circuit to the level sensor in FIG. 14.

In operation, when mercury drop 1124 comes into contact with terminals 1126 and 1127 because the road surface declines toward the left, level sensor 1105 becomes equivalent to a circuit illustrated in FIG. 15A. In that case voltage meter 1140 registers 0 volt, i.e., a low reading. On the other hand, when mercury drop 1124 comes into contact with terminals 1128 and 1129 because the road surface declines toward the right, sensor 1105 becomes equivalent to a circuit illustrated in FIG. 15B. In that case voltage meter 1140 registers V volts, i.e., a high reading.

Figure 16:
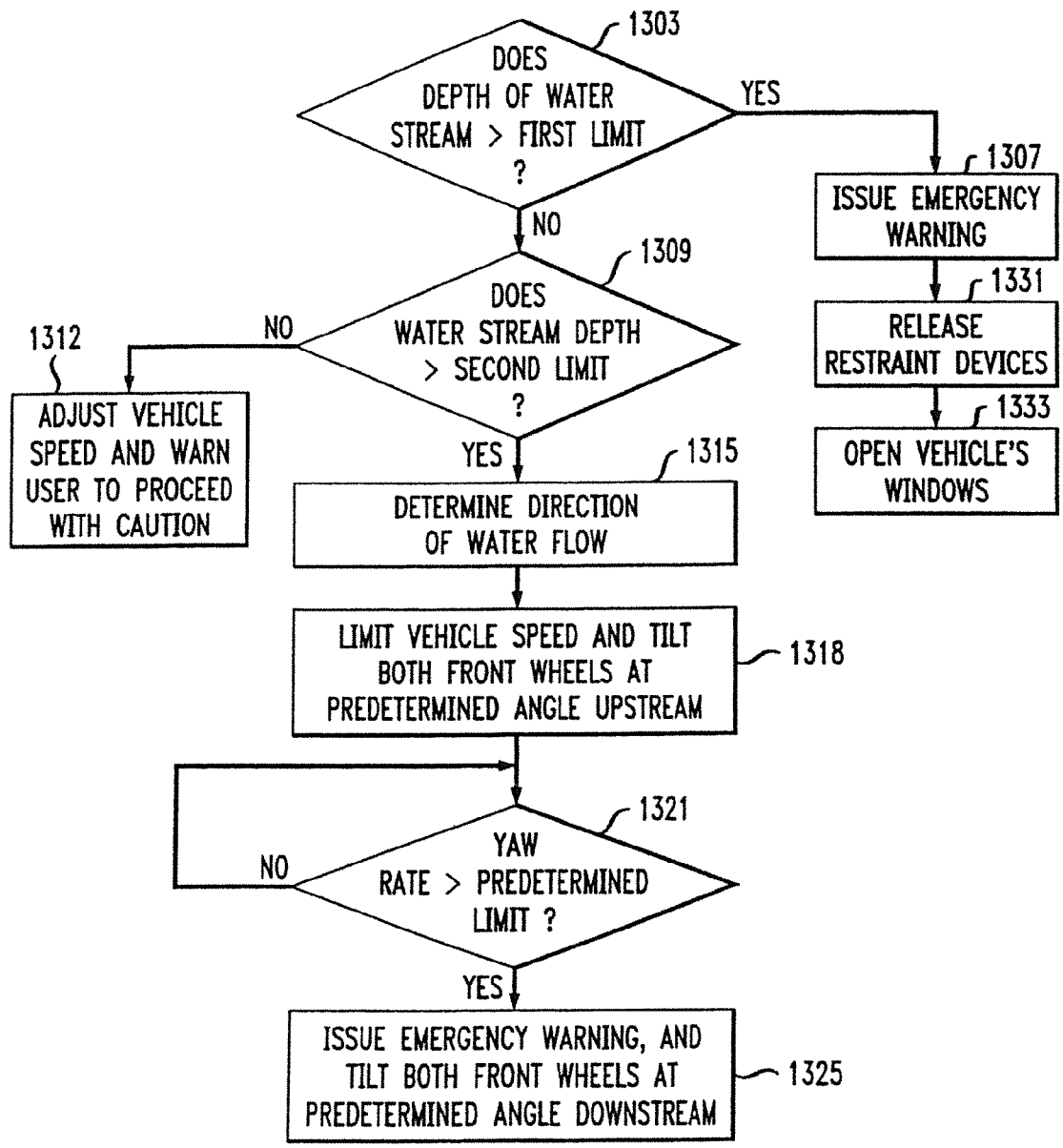
FIG. 16 is a flow chart depicting a process performed by the control system when the vehicle encounters water, in accordance with the invention.

For example, when the vehicle is about to cross a water stream, the aforementioned humidifier detects water because of a high concentration of moisture immediately ahead of the vehicle. As soon as water is detected, the humidifier sends an interrupt signal to processor 103. In response, processor 103 activates the aforementioned sonar to measure the depth of the water stream. Based on the sonar measurement, processor 103 determines whether the depth of the water stream exceeds a first limit corresponding to a deep water situation which calls for emergency measures, as indicated at step 1303 in FIG. 16. If it is positive, processor 103 carries out the emergency measures starting from step 1307 described below. Otherwise, if it is determined that the water stream depth is below the first limit, processor 103 at step 1309 further determines whether the water stream depth is above a second limit which corresponds to a dangerous driving situation. If it is negative, processor 103 adjusts the vehicle speed to avoid hydroplaning, and warns the user to proceed with caution, as indicated at step 1312. Otherwise, if it is positive, processor 103 at step 1315 determines the direction of the water flow using level sensor 1105 described above. That is, the water flows in the direction from right to left if processor 103 receives a low reading from meter 1140, and from left to right if processor 103 receives a high reading from meter 1140. Processor 103 then at step 1318 limits the vehicle speed according to the actual stream water depth, and causes steering subsystem 132 to tilt both front wheels 1107 and 1109 at a predetermined angle upstream against the flow to decrease the chance of having the vehicle lose traction and carried downstream. If forward progress is halted, processor 103 causes shifting into a lower or reverse gear, and gradual application of throttle to gain traction.

At the same time, processor 103 monitors the yaw rate of the vehicle indicative of its lateral stability, which is measured by yaw rate sensor 603. Processor 103 at step 1321 determines whether the yaw rate exceeds a predetermined limit beyond which the lateral stability of the vehicle is jeopardized by the current flow impacting the vehicle. If the yaw rate does not exceed the predetermined limit, processor 103 returns to step 1321, thereby entering a lateral stability monitoring state. Otherwise, if the yaw rate exceeds the predetermined limit, processor 103 at step 1325 issues an emergency warning through audio and video media, and at the same time causes steering subsystem 132 to tilt both front wheels 1107 and 1109 at a predetermined angle downstream to allow the vehicle to travel with the flow, avoiding water drawn into the engine.

In dealing with a deep water situation, processor 103 at aforementioned step 1307 issues an emergency warning through audio and video media, urging the occupants to immediately abandon the vehicle and wear any floatation devices. At step 1331, processor 103 causes safety subsystem 151 to release restraint devices, e.g., seat belts, controlled thereby to free the occupants from being restrained to their seats. At step 1333, processor 103 causes access control subsystem 139 to open the vehicle's windows controlled thereby, allowing the occupants to leave the vehicle through the windows.

It should also be noted that the subject vehicle may broadcast the water encounter experience including the knowledge of the terrain and depth of water experienced, and warnings using communications subsystem 154 (described below) to other nearby vehicles so that they can benefit from such an experience. Indeed, the user of the subject vehicle may be a beneficiary of such knowledge and warnings received from another vehicle just having the water encounter experience ahead of the subject vehicle. The received information may help processor 103 to effectively handle the upcoming water encounter. Alternatively, the same information may be received from another source such as a central computer described below.

Figure 17:
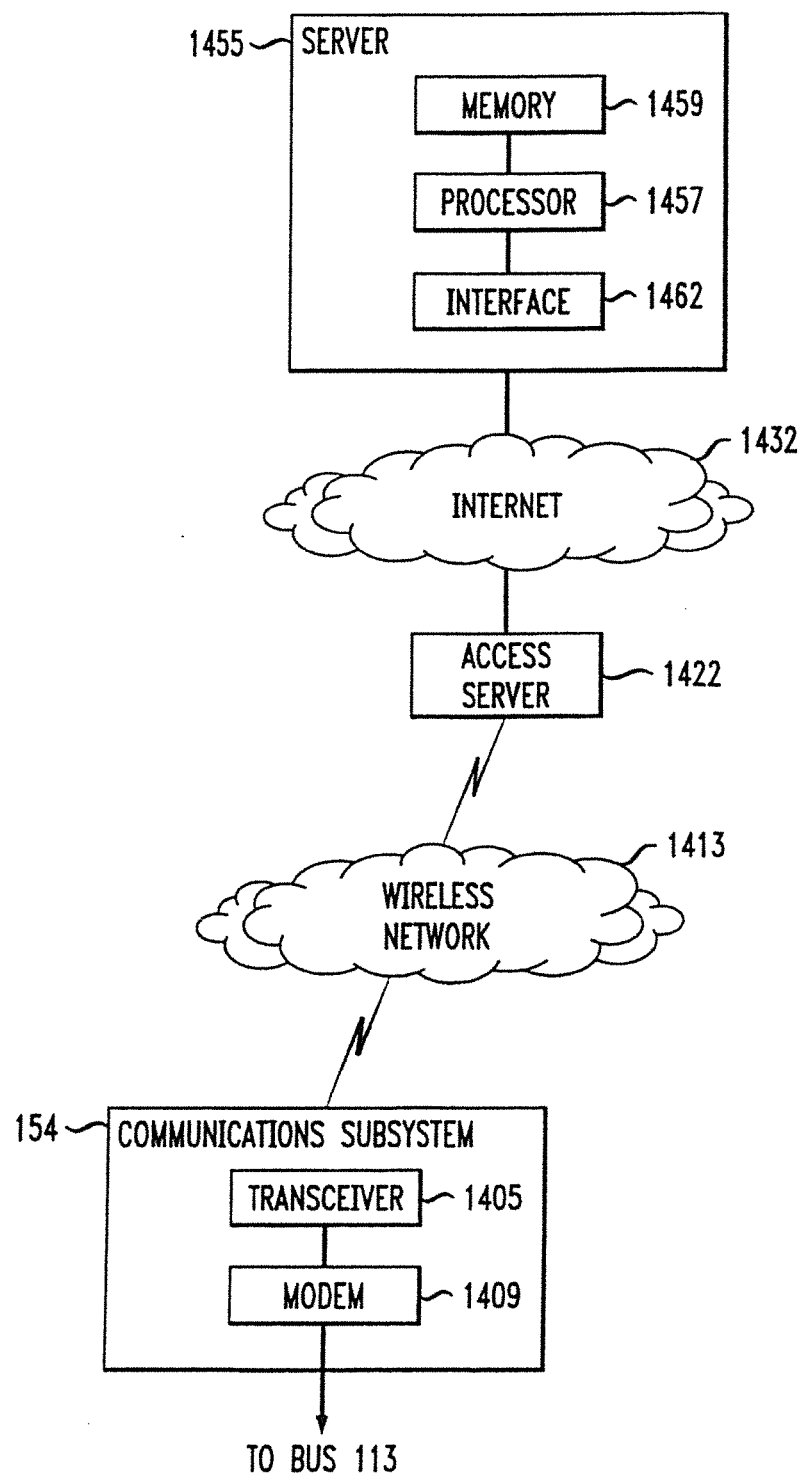
FIG. 17 illustrates an arrangement wherein a communications subsystem in the control system is used to communicate with a remote server.

Communications subsystem 154 is used in the vehicle for communications with remote systems, e.g., server 1455 connected to Internet 1432 in FIG. 17. As shown in FIG. 17, subsystem 154 includes transceiver 1405 and modem 1409. Transceiver 1405 includes, e.g., a wireless phone in the vehicle, for transmitting and receiving information via wireless network 1413, e.g., the well known advanced mobile phone service (AMPS) network, digital AMPS network, personal communications service (PCS) network, global system for mobile communications (GSM) network, paging network, hybrid personal communications network (HPCN), satellite network, microwave network, milliwave network, and auto crash notification (ACN) system, etc. Modem 1409 is used for modulating and demodulating carriers carrying data to and from data channels, e.g., cellular digital packet data (CDPD) channels, in wireless network 1413. For example, for transmitting and receiving data messages to and from server 1455 at a predetermined uniform resource locator (URL), transceiver 1405 establishes a dial-up connection through wireless network 1413 to predetermined access server 1422 which provides access to Internet 1432. It should be noted at this point that server 1422 may not be the only one access server providing the vehicle with the Internet access. It will be appreciated that more access servers similar to server 1422 are geographically distributed for providing effective Internet access.

In accordance with an aspect of the invention, server 1455 is employed to further help vehicle users to operate their vehicles effectively and safely. Server 1455 includes processor 1457, memory 1459 and interface 1462. Server 1455 is connected to Internet 1432 through interface 1462. Memory 1459 contains, among others, a variety of driving programs, which can be downloaded to control systems similar to control system 100 in the subject vehicle. For example, instructed by one such downloaded driving program, processor 103 runs text, demo and voice scripts and quick start information modules, made part of the downloaded program, to demonstrate animated sequences and just-in-time learning sequences for an upcoming driving situation, thereby teaching the user how to maneuver the vehicle to handle the same. Because the memory space of memory 107 is limited while there are myriad driving situations, the driving programs corresponding to such driving situations are advantageously stored in external memory 1457 which is relatively large without overloading memory 107 in the vehicle.

An upcoming driving situation is characterized by weather, traffic and road conditions at a selected distance ahead of the current position of the vehicle, e.g., at least 10 miles ahead in this instance. For example, the information concerning real-time weather, traffic and road surface conditions may be collected using sensors in the road and cameras at intersections. Such information may be continuously fed to a central computer where it is processed and from where it is distributed to vehicles for their utilization. The central computer may be controlled and maintained by a governmental entity, e.g., the department of transportation. Alternatively, each vehicle on the road may serve as a "moving sensor" collecting the weather, traffic and road condition information using radar and infrared sensors therein. The collected information is then transmitted from each vehicle in a wireless manner to the central computer. Of course, the more vehicles that serve as the moving sensor, the more accurate and comprehensive the weather, traffic and road condition information would be.

Thus, when the vehicle traverses a route which is planned by navigation system 205, for each road section ahead on the planned route, processor 105 transmits via communications subsystem 154 a request for weather, traffic and road condition information to the aforementioned central computer. The request includes GPS coordinates from navigation system 205 defining the road section of interest, which is 10 miles from the current vehicle position in this instance. In response, the central computer provides the requested information concerning the particular road section. Such information includes not only the general description of the weather, traffic and road conditions concerning that particular road section, but also detailed description of visibility, road surface condition, and topography and configuration of the road section. If the received information indicates any of the weather and road conditions ahead are hazardous, or the traffic ahead is extremely congested, processor 103 requests navigation system 205 to reroute to avoid any hazardous and congested conditions.

Otherwise, if it is determined that rerouting is unnecessary, but one or more of the weather, traffic and road conditions are unusual, processor 103 issues to server 1455 a request for a driving program. Such a request includes the weather, traffic and road condition information just received from the central computer, and information identifying the vehicle by its year, make and model, e.g., its vehicle identification number (VIN). Based on the received information, processor 1457 in server 1455 selects and downloads to control system 100 one of the driving programs stored in memory 1462 which describes the upcoming driving situation, and the optimal way of handling the situation by the vehicle, given the known limitations and capabilities of the vehicle of that year, make and model.

In an alternative embodiment, processor 103 communicates the GPS coordinates of each road section ahead to server 1455. The latter directly requests information from the aforementioned central computer concerning the weather, traffic and road conditions of the road section ahead. Based on the received information, server 1455 provides advisories to control system 100, including any applicable driving program.

Figure 18:
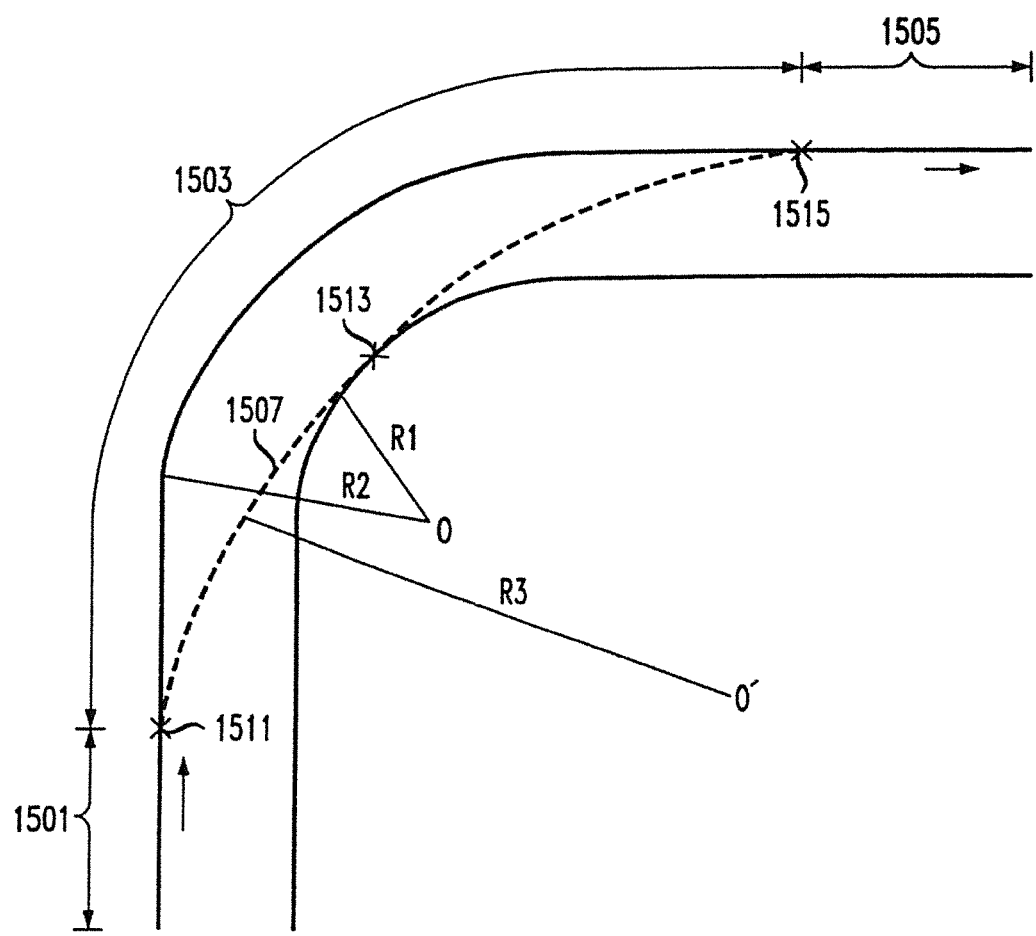
FIG. 18 illustrates handling of a driving situation which involves negotiating a corner, in accordance with the invention.

FIG. 18 illustrates a driving program downloaded to memory 107 from server 1455 and shown on display 117 to demonstrate handling of an upcoming driving situation. Although the downloaded driving program is for demonstration purposes, the driving program corresponds to an actual drivetrain routine stored in memory 107. That is, if the user maneuvers the vehicle in the same manner as described in the driving program, instructed by the drivetrain routine, processor 103 causes electronic transmission/throttle system 210, brake subsystem 125, traction control subsystem 127, steering subsystem 132 and other subsystems to cooperate and effectively achieve the same handling of the driving situation as demonstrated.

The upcoming driving situation in this instance involves driving through road section 1500, which includes straight section 1501, corner 1503 and straight section 1505, given favorable weather and traffic conditions. The curvature of corner 1503 is defined by a first radius R1 and a second radius R2 from center O to an inside road limit and an outside road limit of corner 1503, respectively. In accordance with the downloaded driving program, to get through corner 1503 as efficiently as possible, the user is advised to follow arc 1507 forming part of the largest circle possible connecting turn-in point 1511 close to the outside road limit at the beginning of corner 1503, apex point 1513 close to the inside road limit in the middle of corner 1503, and track-out point 1515 close to the outside road limit at the end of corner 1503. In implementation, the steering wheel should be held straight in section 1501 until the vehicle reaches turn-in point 1511 at the end thereof. At such time, the steering wheel should be turned about 45 degrees and throttle is applied to cause the vehicle to move in a circle, following arc 1507. After the vehicle gets into arc 1507, if the traction allows, additional throttle should be applied to increase the vehicle speed to track arc 1507 with the turning radius R3 from 0'. It should be noted that the higher the speed of the vehicle is when cornering, the larger the turning radius. As the vehicle exits corner 1503, the steering wheel should be gradually unwound. The speed at which the vehicle exits corner 1503 determines how fast the vehicle can reach the efficient speed in section 1505. Also factoring into the speed at which the vehicle exits corner 1503 is the weight and weight distribution of the vehicle and its payload. An increase in weight of the vehicle, caused by added payload, lowers the ground clearance of the vehicle and increase the chance of rollover of the vehicle. Additionally, a shift in payload also increase the chance of the vehicle rolling over.

After the driving program is over, the user is mentally prepared to handle the upcoming driving situation. As the vehicle is approaching the road section in question, processor 103 verifies whether the weather, traffic and road conditions concerning road section 1500 remain more or less the same as before by using detection subsystem 130 and/or by contacting the aforementioned central computer in a manner described above. Where road-side transmitters are installed to broadcast information concerning, e.g., the topography and configuration of upcoming road section 1500 and its road surface condition to guide vehicles therethrough, such information is receptive by communications subsystem 154 and used by processor 103 to control the vehicle in traversing road section 1500. Road-side transmitters may also be installed at aforementioned turn-in point 1511, apex point 1513 and track-out point 1515, respectively. These transmitters may transmit different signals which are receptive by subsystem 154 and which indicate to processor 103 the locations of the respective points to help guide the vehicle through road section 1500. In addition, processor 103 polls each system in the vehicle for a self-diagnostic analysis. The system, when polled, performs an active self-test and reports the test results to processor 103. Processor 103 also polls subsystem 123 for the current driver condition. If the surrounding conditions including weather, traffic and road conditions remain virtually the same as before, and the current vehicle and driver conditions are favorable, processor 103, subject to an intervention by the user, controls (a) electronic transmission/throttle system 210 and brake subsystem 125 to achieve the proper speeds of the vehicle, (b) steering subsystem 132 to achieve the proper turning angles of the steering wheel, and (c) traction control subsystem 127 to afford the proper traction in handling road section 1500 in a manner similar to that previously demonstrated. Otherwise, if the surrounding conditions have significantly changed, the current vehicle condition is unfavorable and/or the driver condition is unfavorable, processor 103 adjusts the speeds of the vehicle accordingly to ensure the safety of the user, or even eases the vehicle onto the shoulder of the road to stop before road section 1500.

It will be appreciated that regardless of whether the vehicle is in operation, for instructional purposes, the user may request from server 1455 to provide driving programs on display 117 from which a user may learn specific driving procedures to handle a car, SUV, mini-van or truck in different driving situations. In addition, the user may utilize user interface 119 to practice and rehearse the driving procedures in the different situations, albeit simulated. The simulation is realized by using multimedia data downloaded from server 1455 as part of the driving program.

Advantageously, with the library of the driving programs available in server 1455, new users can benefit from introductory driving programs in the library for familiarizing himself/herself with basic vehicle functions while experienced users can benefit from relatively advanced driving programs to improve their driving skills, given the different vehicle functions. Thus, a user may selectively download the desired driving programs to memory 107, overwriting any previous driving programs which are no longer desired. Such a just-in-time learning approach is conducive to efficient use of the space of memory 107.

Where the user knows beforehand what driving situations, e.g., off-road, autocross, snow and ice, mud, slippery and wet, mountain, city, traffic, desert situations, are likely to encounter during a trip, it may be advantageous for the user to download the corresponding driving programs before the user starts the trip. Such a download may be accomplished by sending a request including a check list of the desired driving programs to server 1455. Thus, after the desired driving programs are downloaded, the user may practice with the driving programs before the trip, and at the same time those programs are available in memory 107, thereby obviating any delay of downloading them from the server during the actual encounter of the driving situations.

In accordance with another aspect of the invention, when weather and road conditions require use of tire chains, processor 103 communicates instructions to the user on chain use and safety. As mentioned above, an upcoming driving situation is characterized in part by weather, traffic and road conditions at a selected distance ahead of the current position of the vehicle. If processor 103 receives information via communications subsystem 154 indicating that the weather and road conditions ahead may require use of tire chains, the user is advised of this requirement.

Processor 103 receives from communications subsystem 154 information pertaining to road conditions of interest to the user. If the information indicates that chains would be required for the vehicle to traverse the road ahead, processor 103 warns the user of this need via display 117 and user interface 119. If the user has chains available and decides to continue driving, the user may select to have processor 103 instruct him/her on how to put the chains onto the wheels. Such instructions are presented to the user in video and/or text on display 117 and/or synthesized speech through user interface 119. Processor 103 instructs the user to put the chains on all four wheels if four chains are available. In the event that the user only has two chains, processor 103 instructs the user to put the chains on the drive wheels, and indicates which wheels are the drive wheels. Processor 103 accesses memory 107 for information pertaining to which wheels are the drive wheels and presents this information using display 117 and/or user interface 119.

Processor 103 may further instruct the user to lay out the chains in front of the drive wheels and to carefully drive the vehicle onto the chains. Once the chains are in position, processor 103 then instructs the user to stop the vehicle and to get out of the vehicle and wrap the chains around the wheels.

While the vehicle having the chains on is traveling, processor 103 monitors the speed at which the vehicle is moving. If the sensors detect a speed above a predetermined value, for example 30 mph., processor 103 notifies the user, via display 117 and/or user interface 119 that it is dangerous to drive over the predetermined value with chains. If the user does not slow down, or is too slow to respond, or is not cognitive as determined by driver condition subsystem 123, processor 103 operating in connection with brake subsystem 125, slows the vehicle to a speed of equal to or below the predetermined value.

In addition, while the vehicle is traveling, processor 103 operating in connection with communications subsystem 154 receives road conditions. When the road conditions improve to the point where chains are no longer needed, processor 103 notifies the user, via display 117 and/or user interface 119, that it is safe to remove the chains and instructs the user on how to remove the chains.\

In accordance with another aspect of the invention, a user record concerning the user personas and preferences is maintained in memory 1459 of server 1455 in FIG. 17. For example, the user record includes (a) an emergency profile specifying the user's preferences in practicing aggressive driving to handle emergency situations, (b) a commuter profile specifying the user's preferences in practicing time-efficient driving to go to work or business functions, and (c) a vacation profile specifying the user's preferences in practicing leisure driving when the user is on vacation or a shopping trip. In addition, templates may be downloaded from server 1455 to populate display 117 for various types of driving which reflect a selected profile, thereby personalizing the vehicle. Similarly, profiles concerning the user's and passengers' entertainment preferences may be established in server 1455. In that case, entertainment templates for the user and passengers may be downloaded from server 1455 to populate their respective entertainment displays.

It should be noted that system 100 may also provide for an interface for connection with a mobile device such as a personal digital assistant (PDA). Nowadays, a mobile device, e.g., a PALM type PDA, is generally capable of accessing the Internet and other network-type services. Specifically, the mobile device incorporates wireless communications and modem facilities, enabling a user to send and receive electronic mail (e-mail), or to upload and download data through the Internet. Thus, the user may utilize one such mobile device to communicate with server 1455 at the predetermined URL and to access and download, e.g., the above-described driving programs and other information on various vehicle functions pertaining to a designated vehicle. Such programs and information may be transferred to memory 107 when the mobile device is later "docked" or connected to system 100.

In accordance with another aspect of the invention, system 100 monitors the vehicle engine for overheating and notifies the user if such a problem arises. Processor 103 interacts with temperature subsystem 160 in FIG. 19 and performs various tasks according to routines stored in memory 107.

Figure 19:
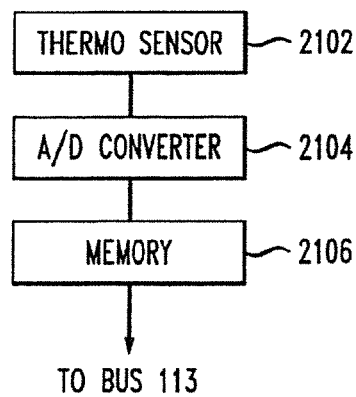
FIG. 19 illustrates is a block diagram of a temperature subsystem in the control system of FIG. 1.

As shown in FIG. 19, temperature subsystem 160 includes thermo sensor 2102 for detecting engine temperature. Subsystem 160 also includes an analog-to-digital (A/D) converter 2104 that converts analog temperature values from sensor 2102 to digital temperature data. The latter is stored in memory 2106.

Instructed by a polling routine for monitoring engine temperature stored in memory 107, processor 103 from time to time collects data from temperature subsystem 160 for analysis. Processor 103 collects data from memory 2106 for analysis at intervals whose length is a function of an engine overheating condition. If the analysis of the data indicates that the vehicle is overheating, or within a danger range, processor 103 polls temperature subsystem 160 at shorter intervals, and thus more frequently, until the condition is rectified.

Figure 20:
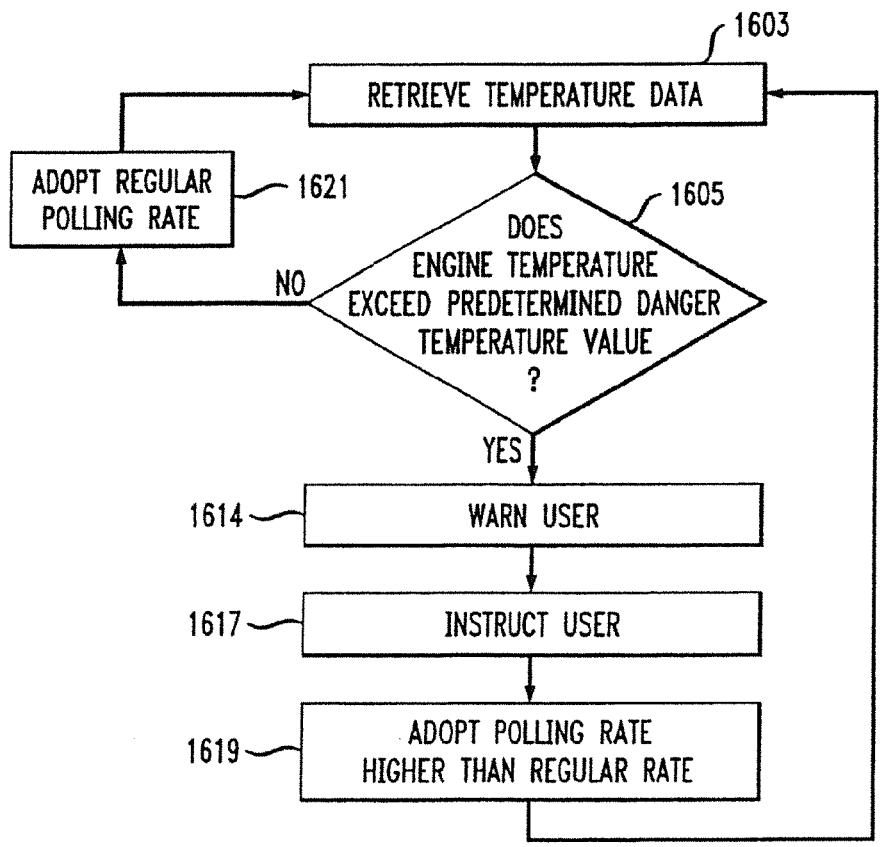
FIG. 20 is a flow chart depicting a process for monitoring the engine temperature in accordance with the invention.

FIG. 20 illustrates the polling routine for monitoring the engine temperature. Instructed by such a routine, processor 103 at step 1603 retrieves temperature data from temperature subsystem 160. Processor 103 determines at step 1605 whether the engine temperature represented by the data exceeds a predetermined danger temperature value. If it is determined that the engine temperature is dangerously high, processor 103 at step 1614 warns the user about the engine overheating condition. At step 1617 processor 103 further instructs the user on how to rectify the condition. For example, instructions such as "Turn on Heater" to assist in cooling down the engine, "Open Windows" to prevent the user from getting too hot inside the car, and "Drive to a Service Station" may be communicated through display 117 and/or user interface 119.

If the temperature data continues to indicate a dangerously high engine temperature, the user may further be instructed to "Increase the Speed of the Vehicle" to help cool the engine. In addition, processor 103 at step 1619 adopts a polling rate higher than a regular polling rate, i.e., analyzing the temperature data at shorter intervals to more closely monitor the situation. If the temperature data indicates that the engine is dangerously close to overheating or has overheated, processor 103 may instruct the user to "Pull Over" immediately at a safe location. Once the user pulls over, as detected by brake subsystem 125, processor 103 communicates instructions on how to cool the temperature of the engine. For example, instructions such as "Spray Water Through the Vehicle Grille to Cool Down the Radiator" may be communicated. While the user is performing the instructions, processor 103 polls temperature subsystem 160 to determine when the engine temperature has dropped to a level that is safe for the user to remove the radiator cap, and add water to the reservoir of the radiator. When a safe temperature level is reached, processor 103 communicates to the user instructions such as "It is Safe to Remove the Radiator Cap" and "Add Water to the Reservoir." As the user performs these instructions, processor 103 continues to poll temperature subsystem 160 for temperature data and compares the data with values that are considered to be acceptable for this particular vehicle. Thus, if it is determined at step 1605 that there is no danger of engine overheating, processor 103 at step 1621 adopts the regular polling rate. Processor 103 may then communicate to the user "It is Safe to Start Driving."

In accordance with another aspect of the invention, a fluid level management subsystem (not shown) is coupled to the vehicle's oil reservoir, brake fluid reservoir, and coolant reservoir for measuring and monitoring the fluid levels. The fluid levels are monitored by comparing the current level with operation level ranges. If one or more of the fluid levels drop below their operation level range, the fluid level management subsystem notifies the user of the problem and instructs the user on how to correct the problem. The fluid level management subsystem also monitors the fluid reservoirs and fluid systems for leaks. A fluid system or reservoir is considered to be leaking if the rate at which the fluid level in the reservoir is changing at a rate greater than a predetermined fluid evaporation/use range. If it is determined that a reservoir or the fluid system is leaking, the user is notified of which fluid system is leaking and is then instructed on how to alleviate or fix the problem.

In accordance with another aspect of the invention, a fan subsystem (not shown) monitors fan operation and air flow through the vehicle's radiator. The fan subsystem is coupled to the fan so that the rotation of the fan may be monitored. If the rotation of the fan stops or rotates at a rate different than a predetermined rate range, the fan subsystem notifies the user of the problem and instructs the user on how to alleviate or fix the problem. The fan subsystem also monitors the rate of airflow through the radiator and notifies the user if the rate of air flow indicates that the radiator may be obstructed or partially obstructed.

In accordance with another aspect of the invention, a belt subsystem (not shown) monitors the vehicle's alternator for belt slippage. If the alternator's belt is slipping, the alternator may fail to charge the vehicle's battery, resulting in a depletion of the battery charge. The belt subsystem is coupled to the alternator's shaft and measures the rate at which the alternator is rotating. The rate at which the alternator is rotating is compared with a predetermined rate range, to determine whether the alternator is rotating faster or slower than the predetermined range allows. If the alternator is rotating outside the predetermined range, for example, too slowly, then the user is notified that the alternator belt is slipping and should be changed or repaired.

Figure 21:
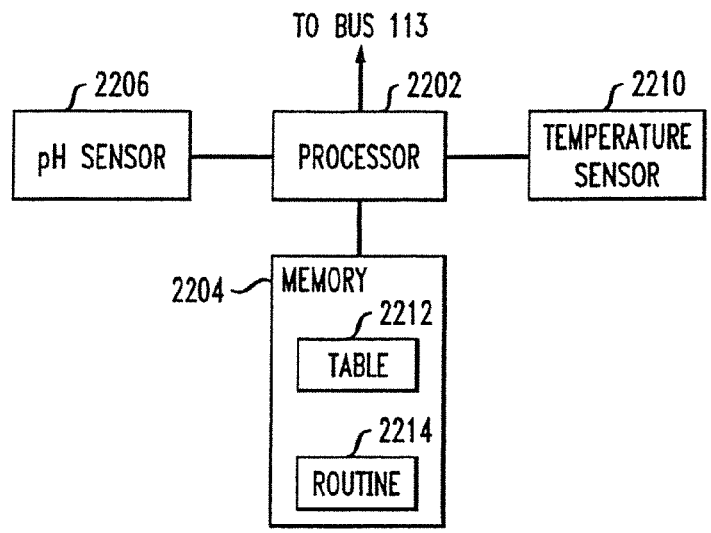
FIG. 21 is a block diagram of a radiator subsystem in the control system of FIG. 1.

In accordance with another aspect of the invention, radiator subsystem 163 is used for determining the proportion of coolant (e.g., antifreeze) to water in the vehicle's radiator. As shown in FIG. 21, radiator subsystem 163 includes pH sensor 2206 for measuring the pH level of the solution in the radiator. Sensor 2206 includes an electrode submerged in the solution. Subsystem 163 also includes temperature sensor 2210 for measuring temperature of the solution, processor 2202, and memory 2204 containing routine 2214 and table 2212. Table 2212 relates pH levels of the solution, indicative of the concentrations of the coolant, to the safe temperature range values, for an essentially constant volume. Routine 2214 is used to monitor the proper proportion of the coolant to water in the radiator for safe operation of the vehicle at a given temperature range.

Figure 22:
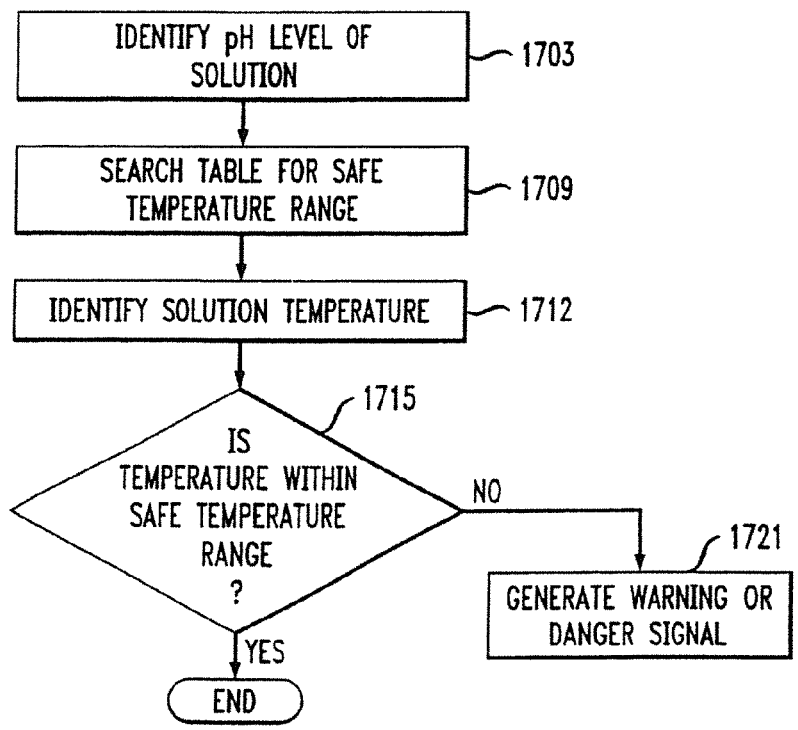
FIG. 22 is a flow chart depicting a process for monitoring the temperature and concentration of a radiator fluid in accordance with the invention.

FIG. 22 illustrates routine 2214. Instructed by such a routine, processor 2202 at step 1703 identifies the pH level of the solution in the radiator using sensor 2206, which is indicative of a concentration of the coolant in the solution. Processor 2202 at step 1709 searches table 2212 for a safe temperature range corresponding to the pH level just determined. Processor 2202 at step 1712 identifies the solution temperature using temperature sensor 2210. Processor 2202 at step 1715 determines whether the temperature just identified is within the safe temperature range. If so, routine 2214 comes to an end. Otherwise, processor 2202 at step 1721 generates a warning or danger signal. Such a warning may be displayed on display 117, and accompanied by an audible alert through user interface 119.

Additionally, the vehicle's odometer is a source of data for use in determining whether certain maintenance is required if the vehicle has traveled a predetermined mileage. If the vehicle has traveled the predetermined mileage, processor 103 sends radiator maintenance information to the user via display 117 or user interface 119. The maintenance information may concern preventive measures that may be taken to prevent vehicle overheating. Examples of maintenance information includes: "Change Radiator Cap", "Change Thermostat", "Check if Radiator Hoses Feel Soft and Replace", and "Install an Auxiliary Transmission Cooler."

In accordance with another aspect of the invention, operating as a short range altimeter, vehicle clearance subsystem 169 determines current vehicle ground clearance which may vary with the load on the vehicle. Subsystem 169 includes one or more transceivers disposed on different points of the vehicle. These transceivers are used to emit signals to, and detect signals reflected from, the ground. Processor 103 determines the current vehicle ground clearance based on a time lag between emission of a signal and receipt of a reflected version thereof. It should be realized that vehicle clearance subsystem 169 may be designed to operate in various frequency ranges such as radar, sonar, UHF, or microwave.

Object profile subsystem 172 is used to determine the profiles of objects in front of and behind the vehicle, which may be debris or obstacles on the road, curbs, inclines, etc. Subsystem 172 includes transceivers for emitting signals to, and receiving signals reflected from, one such object. The reflected signals are analyzed by processor 103 to determine the profile of the object including its dimensions. The transceivers are positioned in the front and back of the vehicle. It should be realized that subsystem 172 may be designed to operate in various frequency ranges such as radar, sonar, UHF, or microwave.

Figure 23:
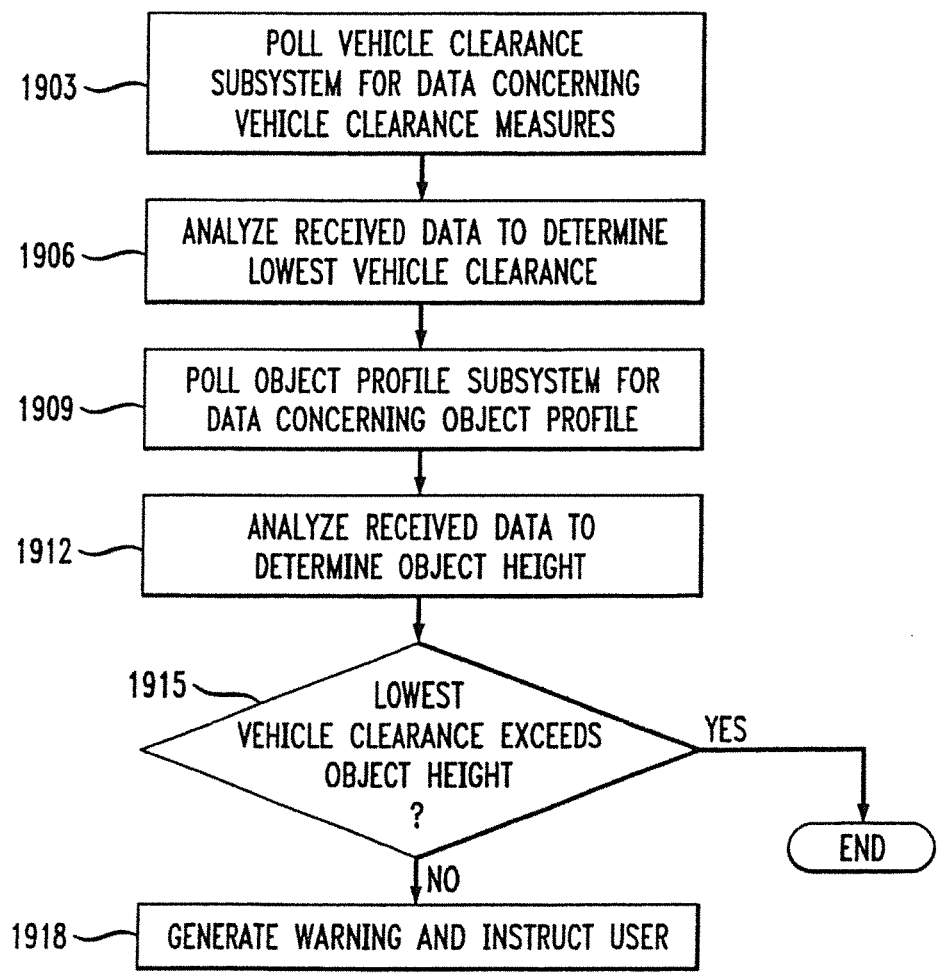
FIG. 23 is a flow chart depicting a process for monitoring vehicle clearance in accordance with the invention.

FIG. 23 illustrates a safety routine for determining whether the vehicle would clear an object in its path. Such a safety routine is triggered when one such object is detected, e.g., by detection subsystem 130. Referring to FIG. 23, instructed by the safety routine, processor 103 at step 1903 polls vehicle clearance subsystem 169 for data concerning vehicle clearance measures at different points of the vehicle. Processor 103 at step 1906 analyzes the received data to determine, of the measures, the lowest vehicle clearance from the ground. Processor 103 at step 1909 polls object profile subsystem 172 for data concerning a profile of the object. At step 1912, processor 103 analyzes the received data to determine the height of the object. Processor 103 at step 1915 determines whether the lowest vehicle clearance exceeds the height of the object. If so, the routine comes to an end. Otherwise, processor 103 at step 1918 generates a warning to be shown on display 117 and/or announced through user interface 119, and instructs the user to either negotiate around the object or stop.

If the user decides to negotiate around the object, a shift in weight of the vehicle would be detected by traction control subsystem 127, which detects lateral acceleration. In response to a detection of such lateral acceleration, processor 103 may adjust transmission/throttle system 210, in cooperation with other subsystems, to slow the vehicle down. Processor 103 may also cause the camber of the tires to be adjusted to increase their CF and thus their traction.

If the user fails to respond to a warning of a detected object, processor 103 causes braking of the vehicle using brake subsystem 125 to slow the vehicle down. At the same time, processor 103 causes steering subsystem 132, guided by navigation system 205 and radar and/or infrared sensors in detection subsystem 130, to steer the vehicle onto the shoulder of the road.

Moreover, processor 103 polls driver condition subsystem 123 for the current driver condition and determines if the driver is mentally prepared to handle an upcoming driving situation, such as an object in the path of the vehicle. As the vehicle approaches the object, processor 103 verifies whether the vehicle can clear the object and verifies whether the driver condition is favorable or unfavorable. If driver condition is unfavorable, processor 103 adjusts the speed and the brakes of the vehicle to ensure the safety of the driver, or eases the vehicle onto the shoulder of the road and stops the vehicle.

In this illustrative embodiment, detection subsystem 130 is also used to determine positions of objects located at the sides of the vehicle, which includes transceivers for emitting signals and detecting the reflected versions thereof. In a well known manner, based on the time lags between emission of the signals and the detection of the reflected signals, processor 103 determines locations of any objects (or object coordinates) around the vehicle. In this instance the transceivers operate within the radar spectrum. It should be realized that subsystem 130 may be designed to operate in other frequency ranges such as sonar, UHF or microwave. The transceivers may be placed in various locations around the vehicle. For example, they may be placed near the side front and rear bumpers, where they can detect the location of objects such as other vehicles, curbs, poles, etc.

In accordance with another aspect of the invention, subsystem 130 is used to assist a user to drive around an object according to a turn assistance routine. This routine is especially useful when the vehicle is lengthy which, e.g., has a trailer attached thereto. For example, as part of the routine, the user is requested to enter the length and width measurements of the trailer onto system 100 through user interface 119 before towing the trailer. After the length and width data is entered, processor 103 stores the data in memory 107, which may be used later to determine a safe turning angle for the vehicle and trailer. Additional information such as trailer axle location, tongue weight, length between the tongue and trailer axle, overhang, steering inputs, and trailer wheel diameter which may affect the determination of the safe turning angle may be requested from the user as well. Given a lateral distance between the vehicle/trailer and the object (i.e., distance of the object measured perpendicularly from the side of the vehicle/trailer), a safe turning angle is realized when the distance is determined which the vehicle and trailer must travel beyond the object before a turn can be completed without the vehicle and/or frailer hitting the object.

Figure 24:
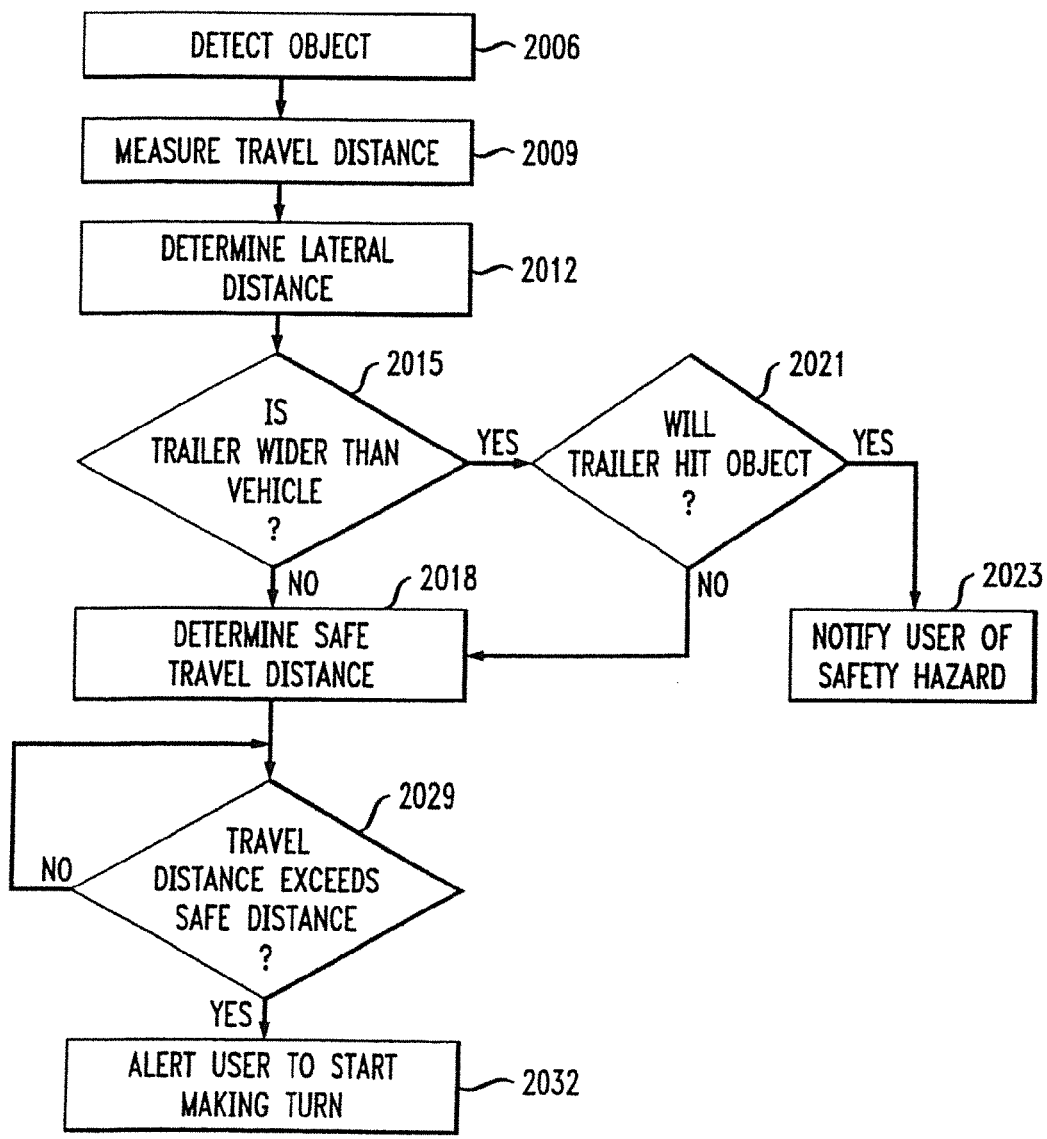
FIG. 24 is a flow chart depicting a process for assisting a user to make a turn in accordance with the invention.

In this example, processor 103 utilizes the length and width data of the frailer, length and width data of the vehicle which is known a priori, and the object coordinates provided by subsystem 130 to determine the safe turning angle. The turn assistance routine illustrated in FIG. 24 is invoked by the user's putting on a turn signal in advance of an upcoming turn. Referring to FIG. 24, as the vehicle passes an object to be avoided in the upcoming turn, processor 103 at step 2006 detects the object at the front side of the vehicle. Processor 103 at step 2009 polls the vehicle's odometer to measure the travel distance the vehicle and trailer has been covering since the time of detecting the object. Using data from subsystem 130, processor 103 at step 2012 determines the lateral distance the object is from the vehicle. At step 2015, processor 103 compares the width of the vehicle with the width of the trailer to determine which one is wider. Knowing how much wider or narrower the width of the trailer is, relative to the vehicle, processor 103 at step 2021 determines whether the trailer will hit the object in passing. This is determined by comparing the distance the trailer extends from the side of the vehicle with the lateral distance determined at step 2012. If it is determined that the trailer will hit the object, processor 103 at step 2023 immediately notifies the user of this safety hazard.

Otherwise, if it is determined that the trailer will not hit the object, processor 103 at step 2018 determines a safe travel distance the vehicle and trailer must cover before starting to turn to avoid hitting the object. This determination is based on the combined length of the vehicle and trailer, and the lateral distance between the object and vehicle or between the object and trailer, whichever is shorter. The trailer axle location, tongue weight, length between the tongue and trailer axle, overhang, steering inputs, and trailer wheel diameter may also be taken into account when determining the safe travel distance. Processor 103 at step 2029 determines whether the travel distance, measured by the odometer since the object was detected at the front side of the vehicle, exceeds the safe distance.

As soon as it is determined that the travel distance exceeds the safe distance, processor 103 at step 2032 alerts the user to start making the turn. For example, processor 103 may prompt the user to make the turn through use of audio, video and/or textual messages.

The foregoing merely illustrates the principles of the invention. It will thus be appreciated that those skilled in the art will be able to devise numerous other systems which embody the principles of the invention and are thus within its spirit and scope.

For example, system 100 is illustratively used in a vehicle which generally encompasses mobile equipment, e.g., an automobile, a truck, a sports utility vehicle (SUV), a tractor, a Jeep, a military vehicle, a boat, an airplane, etc.

In addition, system 100 can be readily modified to function on various network platforms. It should be realized that multiple networks may be used, instead, with each providing its own scheduling routine, and one or more of the following routines: a time slicing routine, a polling routine, and an interrupt routine.

Moreover, a communications event manager may be incorporated in system 100. The communications event manager may control scheduling of required tasks between processor 103 and the various subsystems.

Finally, although system 100, as disclosed, is embodied in the form of various discrete functional blocks, the system could equally well be embodied in an arrangement in which the functions of any one or more of those blocks or indeed, all of the functions thereof, are realized, for example, by one or more appropriately programmed processors or devices.

The invention claimed is:

1. A method for use in a system allowing for personalizing a vehicle, comprising:
    collecting information about a user from the user via a user interface, the information comprising user display preferences, collecting information from the user comprising:
        allowing selection by the user of a first one of a plurality of dashboard display templates;
        establishing the first dashboard display template as a user display preference associated with a first user profile that is maintained in a memory, the first user profile comprising a first plurality of user preferences;
        allowing selection by the user of a second one of a plurality of dashboard display templates; and
        establishing the second dashboard display template as a user display preference associated with a second user profile that is maintained in the memory, the second user profile comprising a second plurality of user preferences;
    selecting the first user profile during a first mode of driving, and selecting the second user profile during a second mode of driving;
    displaying data concerning one or more vehicle components on a dashboard display device;
    if the first user profile is selected, configuring display on the dashboard display device in accordance with the first dashboard display template; and
    if the second user profile is selected, configuring display on the dashboard display device in accordance with the second dashboard display template.

2. The method of claim 1, wherein the first mode of driving includes leisure driving and the second mode of driving includes non-leisure driving.

3. The method of claim 2 additionally comprising downloading the first and second display templates from a server that is remote from the vehicle to a vehicle control system of the vehicle.

4. The method of claim 3, wherein downloading the first and second display templates comprises downloading the first and second display templates from the server to a mobile device, removably connecting the mobile device with the vehicle control system, downloading the first and second display templates from the mobile device to the vehicle control system, and removing the mobile device from connection with the vehicle control system.

5. The method of claim 4 additionally comprising downloading instructional materials concerning vehicle operation from the server to the vehicle control system via the mobile device when the mobile device is connected with the vehicle control system.

6. The method of claim 4, wherein the mobile device communicates with the server through the Internet.

7. The method of claim 6, wherein the mobile device communicates with the server via wireless communications.

8. The method of claim 1 additionally comprising downloading the first and second display templates from a server that is remote from the vehicle to a vehicle control system of the vehicle.

9. The method of claim 8, wherein downloading the first and second display templates comprises downloading the first and second display templates from the server to a mobile device, docking the mobile device with the vehicle control system, downloading the first and second display templates from the mobile device to the vehicle control system, and undocking the mobile device from the vehicle control system.

10. The method of claim 1 additionally comprising downloading data via a wireless communication from a server that is remote from the vehicle to a handheld mobile device, selectively connecting the handheld mobile device with a vehicle control system of the vehicle, and downloading the data from the handheld mobile device to the vehicle control system.

11. The method of claim 10, wherein the data comprises multimedia content.

12. The method of claim 11, wherein the data comprises instructional content.

13. The method of claim 10 additionally comprising disconnecting the handheld mobile device from the vehicle control system.

14. The method of claim 13, comprising downloading the data to the handheld mobile device while the handheld mobile device is not connected to the vehicle control system.

15. The method of claim 1, wherein the user interface comprises a touchscreen display apparatus.

* * * * *